(12) United States Patent
McDonald et al.

(10) Patent No.: US 9,132,085 B2
(45) Date of Patent: Sep. 15, 2015

(54) COMPOSITIONS AND METHODS FOR TREATING POST-OPERATIVE PAIN USING CLONIDINE AND BUPIVACAINE

(75) Inventors: Phillip E. McDonald, Plymouth, MN (US); Amira Wohabrebbi, Memphis, TN (US); Christopher M. Hobot, Tonka Bay, MN (US); Vanja M. King, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1100 days.

(21) Appl. No.: 12/420,110

(22) Filed: Apr. 8, 2009

(65) Prior Publication Data

US 2009/0263321 A1    Oct. 22, 2009

Related U.S. Application Data

(60) Provisional application No. 61/046,234, filed on Apr. 18, 2008.

(51) Int. Cl.
| | |
|---|---|
| *A61K 51/00* | (2006.01) |
| *A61K 9/00* | (2006.01) |
| *A61K 9/20* | (2006.01) |

(52) U.S. Cl.
CPC ............. *A61K 9/0024* (2013.01); *A61K 9/204* (2013.01)

(58) Field of Classification Search
None
See application file for complete search history.

(56) References Cited

U.S. PATENT DOCUMENTS

| | | | |
|---|---|---|---|
| 3,190,802 A | 6/1965 | Zeile et al. | |
| 3,020,660 A | 8/1965 | Zeile et al. | |
| 4,624,255 A | 11/1986 | Schenck | |
| 4,765,974 A | 8/1988 | Tokuda et al. | |
| 4,863,457 A | 9/1989 | Lee | |
| 5,175,052 A | 12/1992 | Tokuda et al. | |
| 5,447,947 A | 9/1995 | Campbell | |
| 5,484,607 A | 1/1996 | Horacek | |
| 5,522,844 A | 6/1996 | Johnson | |
| 5,540,912 A | 7/1996 | Roorda et al. | |
| 5,626,838 A | 5/1997 | Cavanaugh | |
| 5,635,204 A | 6/1997 | Gevirtz et al. | |
| 5,759,583 A | 6/1998 | Iwamoto | |
| 5,801,188 A | 9/1998 | Hassenbusch, III et al. | |
| 5,868,789 A | 2/1999 | Huebner | |
| 5,869,100 A | 2/1999 | Horacek | |
| 5,942,241 A | 8/1999 | Chasin | |
| 5,942,503 A | 8/1999 | Jung et al. | |
| 5,942,530 A | 8/1999 | Panetta et al. | |
| 5,945,416 A | 8/1999 | Shannon et al. | |
| 5,980,927 A | 11/1999 | Nelson et al. | |
| 6,030,642 A | 2/2000 | Horacek | |
| 6,069,129 A | 5/2000 | Sandberg | |
| 6,147,102 A | 11/2000 | Borgman | |
| 6,179,862 B1 | 1/2001 | Sawhney | |
| 6,248,345 B1 | 6/2001 | Goldenheim | |
| 6,287,588 B1 | 9/2001 | Shih | |
| 6,326,020 B1 | 12/2001 | Kohane | |
| 6,331,311 B1 | 12/2001 | Brodbeck | |
| 6,417,184 B1 | 7/2002 | Ockert | |
| 6,428,804 B1 | 8/2002 | Suzuki | |
| 6,461,631 B1 | 10/2002 | Dunn | |
| 6,524,607 B1 | 2/2003 | Goldenheim | |
| 6,534,048 B1 | 3/2003 | Borgman | |
| 6,534,081 B2 | 3/2003 | Goldenheim | |
| 6,589,549 B2 | 7/2003 | Shih | |
| 6,630,155 B1 | 10/2003 | Chandrashekar | |
| 6,632,456 B1 | 10/2003 | Sawhney | |
| 6,756,058 B2 | 6/2004 | Brubaker | |
| 6,773,714 B2 | 8/2004 | Dunn | |
| 6,921,541 B2 | 7/2005 | Chasin | |
| 6,974,462 B2 | 12/2005 | Sater | |
| 6,992,110 B2 | 1/2006 | Kranzler et al. | |
| 7,144,412 B2 | 12/2006 | Wolf | |
| 7,166,570 B2 | 1/2007 | Hunter | |
| 7,220,281 B2 | 5/2007 | Lambrecht | |
| 7,229,441 B2 | 6/2007 | Trieu | |
| 7,235,043 B2 | 6/2007 | Gellman | |
| 7,287,983 B2 | 10/2007 | Han | |
| 7,318,840 B2 | 1/2008 | McKay | |
| 7,329,259 B2 | 2/2008 | Cragg | |
| 7,345,065 B2 | 3/2008 | Gil et al. | |
| 7,361,168 B2 | 4/2008 | Makower | |
| 7,367,978 B2 | 5/2008 | Drewry | |
| 7,507,398 B2 | 3/2009 | Rabinowitz et al. | |
| 7,524,812 B2 | 4/2009 | Ellis et al. | |

(Continued)

FOREIGN PATENT DOCUMENTS

| | | |
|---|---|---|
| IE | WO 2005000278 A1 * | 1/2005 |
| WO | 9641616 A1 | 12/1996 |

(Continued)

OTHER PUBLICATIONS

Moniche et al. in Anesthesiology 2002, 96, 725-741.*

(Continued)

*Primary Examiner* — Dennis Heyer
*Assistant Examiner* — Daniel M Podgorski
(74) *Attorney, Agent, or Firm* — Sorell Lenna & Schmidt LLP

(57) ABSTRACT

Effective treatments of pain that accompanies post-operative surgeries are provided. Through the administration of an effective amount of a combination of bupivacaine and clonidine at or near a target site, one can alleviate or prevent pain. This administration of bupivacaine and clonidine or pharmaceutically acceptable salts thereof is particularly useful following surgery.

18 Claims, 13 Drawing Sheets

(56) References Cited

U.S. PATENT DOCUMENTS

| | | |
|---|---|---|
| 2002/0009454 A1 | 1/2002 | Boone |
| 2002/0058656 A1 | 5/2002 | Ockert |
| 2002/0090398 A1 | 7/2002 | Dunn |
| 2002/0094998 A1 | 7/2002 | Burke et al. |
| 2003/0022926 A1 | 1/2003 | Lavand'Homme |
| 2003/0185873 A1 | 10/2003 | Chasin |
| 2003/0204191 A1 | 10/2003 | Sater |
| 2003/0224033 A1 | 12/2003 | Li |
| 2004/0028726 A1 | 2/2004 | Fischer et al. |
| 2004/0072799 A1 | 4/2004 | Li |
| 2004/0082540 A1 | 4/2004 | Hermida Ochoa |
| 2004/0101582 A1 | 5/2004 | Wolicki |
| 2004/0109893 A1 | 6/2004 | Chen |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter |
| 2005/0175709 A1 | 8/2005 | Baty |
| 2005/0177135 A1* | 8/2005 | Hildebrand et al. ....... 604/890.1 |
| 2005/0186261 A1 | 8/2005 | Avelar |
| 2005/0197293 A1 | 9/2005 | Mellis |
| 2006/0074422 A1 | 4/2006 | Story |
| 2006/0106361 A1 | 5/2006 | Muni |
| 2006/0148903 A1 | 7/2006 | Burch |
| 2006/0183786 A1 | 8/2006 | Wang |
| 2006/0189944 A1 | 8/2006 | Campbell |
| 2006/0228391 A1 | 10/2006 | Seyedin |
| 2006/0253100 A1 | 11/2006 | Burright et al. |
| 2007/0156180 A1 | 7/2007 | Jaax |
| 2007/0185497 A1 | 8/2007 | Cauthen |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos |
| 2007/0253994 A1 | 11/2007 | Hildebrand |
| 2008/0091207 A1 | 4/2008 | Truckai |
| 2008/0152709 A1 | 6/2008 | Bortz |
| 2008/0171075 A1 | 7/2008 | Ozturk et al. |

FOREIGN PATENT DOCUMENTS

| | | | | |
|---|---|---|---|---|
| WO | WO 96/41616 | * | 12/1996 | ............ A61K 9/14 |
| WO | WO2003005961 A2 | | 1/2003 | |
| WO | WO2004091540 A2 | | 10/2004 | |
| WO | WO2005034998 A2 | | 4/2005 | |
| WO | 2005120435 A2 | | 12/2005 | |
| WO | 2006011915 A1 | | 2/2006 | |
| WO | 2006022611 A2 | | 3/2006 | |
| WO | 2006101540 A1 | | 9/2006 | |
| WO | WO2007005177 A1 | | 1/2007 | |
| WO | 2008079868 A1 | | 7/2008 | |
| WO | 2009100441 A2 | | 8/2009 | |

OTHER PUBLICATIONS

Al Malyan et al. in the Journal of Craniofacial Surgery (17,(2) 302-313, 2006).*
Santovena et al. in Biomaterials 25 (2004) 925-931.*
'Sensor One dynecm2 conversion table' in www.sensorone.co.uk/pressure-measurement-glossary/, retreived from internet Sep. 13, 2011.*
Kim et al. (International Journal of Pharmaceutics, 2005, 304, 165-177).*
Aantaa, Riku, MD, PhD, Alpha2-Agonists, Sedatives or Analgesics, Department of Anesthesiology and Intensive Care, University of Turku, Finland, Apr. 15, 2009.
QLT, Inc., Atrigel Drug Delivery Platform, Jul. 2006.
www.medscape.com, Pharmacological Approaches.
Moberg-Wolff, Spasticity, pp. 1-15, Dec. 21, 2007.
Moore, Daniel P., M.D., Helping Your Patients With Spasticity Reach Maximal Function, vol. 104, No. 2, Aug. 1998, Postgraduate Medicine.
International Search Report and Written Opinion for Application PCT/2009/040453 mailed Jul. 1, 2010.
Classen, et al., Stability of Admixture Containing Morphine Sulfate, Bupivacaine Hydrochloride, and Clonidine Hydrochloride in an Implantable Infusion System, vol. 28, No. 6, Dec. 2004, Journal of Pain and Sympton Management, New York, NY, pp. 603-611, XP004672214, ISSN: 0885-3924, the whole document.

* cited by examiner

COMPOSITIONS AND METHODS FOR TREATING POST-OPERATIVE PAIN USING CLONIDINE AND BUPIVACAINE

This application claims the benefit of the filing date of Provisional Application No. 61/046,234, filed Apr. 18, 2008, entitled "Compositions And Methods For Treating Post-Operative Pain Using Clonidine And Bupivacaine." This entire disclosure is hereby incorporated by reference into the present disclosure.

BACKGROUND

Pain is typically experienced when the free nerve endings of pain receptors are subject to mechanical, thermal, chemical or other noxious stimuli. These pain receptors can transmit signals along afferent neurons to the central nervous system and then to the brain. When a person feels pain, any one or more of a number of problems can be associated with this sensation, including but not limited to reduced function, reduced mobility, complication of sleep patterns, and decreased quality of life.

The causes of pain include inflammation, injury, disease, muscle spasm and the onset of a neuropathic event or syndrome. By way of example, inflammatory pain can occur when tissue is damaged, as can result from surgery or an adverse physical, chemical or thermal event or from infection by a biologic agent. When a tissue is damaged, a host of endogenous pain inducing substances, for example, bradykinin and histamine can be released from the injured tissue. The pain inducing substances can bind to receptors on the sensory nerve terminals and thereby initiate afferent pain signals. After activation of the primary sensory afferent neurons, the projection neurons may be activated. These neurons carry the signal via the spinothalamic tract to higher parts of the central nervous system. Inflammatory pain is generally reversible and may subside when the injured tissue has been repaired or the pain inducing stimuli is removed.

When a patient undergoes surgery, there is an increased likelihood that absent the use of analgesics, pain will be felt during and/or after surgery. Thus, this pain, including the post-operative pain is to a degree predictable with respect to whom it most likely will affect, is most likely to occur within a finite window of time, and is localized to a site at or near the site of a surgical procedure.

One known class of pharmaceuticals to treat post-operative pain is opioids. This class of compounds is well-recognized as being among the most effective type of drugs for controlling post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Further, because of these side-effects, physicians typically limit the administration of opioids to within the first twenty-four hours post-surgery. Thus, it would be preferable to use non-narcotic drugs that deliver direct, localized pain control at a surgical site.

One pharmaceutical that is known to the medical profession is clonidine, which is widely recognized as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$) may be represented by the following chemical structure:

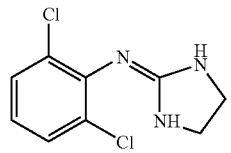

Another pharmaceutical that is known to the medical profession is bupivacaine, which is widely recognized as a local anesthetic for infiltration, nerve block, epidural and intrathecal administration. In general, bupivacaine, also referred to as 1-butyl-N-(2,6-dimethylphenyl)piperidine-2-carboxamide ($C_{18}H_{28}N_2O$)) may be represented by the following structure:

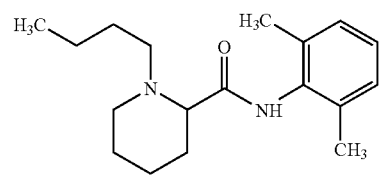 [SMILES: CCCCN1CCCCC1C(=O)Nc1c(C)cccc1C]

Because of the unique manifestation and relatively predictable risks for post-operative pain, there is a need for effective treatments for post-operative pain, including methods and compositions to alleviate or to treat this pain.

SUMMARY

Compositions are provided comprising bupivacaine or its pharmaceutically acceptable salt in combination with clonidine or its pharmaceutically acceptable salt that are administered in order to relieve pain after surgery. Methods for administering these compositions are also provided. When administered in an effective amount, particularly in sustain release formulations, the compositions and methods may provide effective treatments for post-operative pain.

According to one embodiment there is a drug depot comprising: (a) a therapeutically effective amount of bupivacaine or a pharmaceutically acceptable salt thereof; and (b) a therapeutically effective amount of clonidine or a pharmaceutically acceptable salt thereof.

According to another embodiment there is a method of treating or preventing postoperative pain, the method comprising administering a therapeutically effective amount of bupivacaine or a pharmaceutically acceptable salt thereof and clonidine or a pharmaceutically acceptable salt thereof to a target tissue site beneath the skin, wherein the drug depot releases an effective amount of the bupivacaine or pharmaceutically acceptable salt thereof and the clonidine or pharmaceutically acceptable salt thereof over a period of 3 to 12 days.

According to another embodiment there is a method of inhibiting postoperative pain, the method comprising delivering one or more biodegradable drug depots comprising a therapeutically effective amount of bupivacaine or a pharmaceutically acceptable salt thereof and clonidine or a pharmaceutically acceptable salt thereof to a target tissue site beneath the skin before, during or after surgery, wherein the drug depot releases an effective amount of bupivacaine or pharmaceutically acceptable salt thereof and the clonidine or pharmaceutically acceptable salt thereof over a period of 3 to 12 days.

According to another embodiment there is an implantable drug depot useful for preventing or treating postoperative pain in a patient in need of such treatment, the implantable drug depot comprising a therapeutically effective amount of bupivacaine or a pharmaceutically acceptable salt thereof and clonidine or a pharmaceutically acceptable salt thereof, the drug depot being implantable at a site beneath the skin to prevent or treat postoperative pain, wherein the drug depot releases an effective amount of the bupivacaine or pharmaceutically acceptable salt thereof and the clonidine or pharmaceutically acceptable salt thereof over a period of 3 to 12 days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
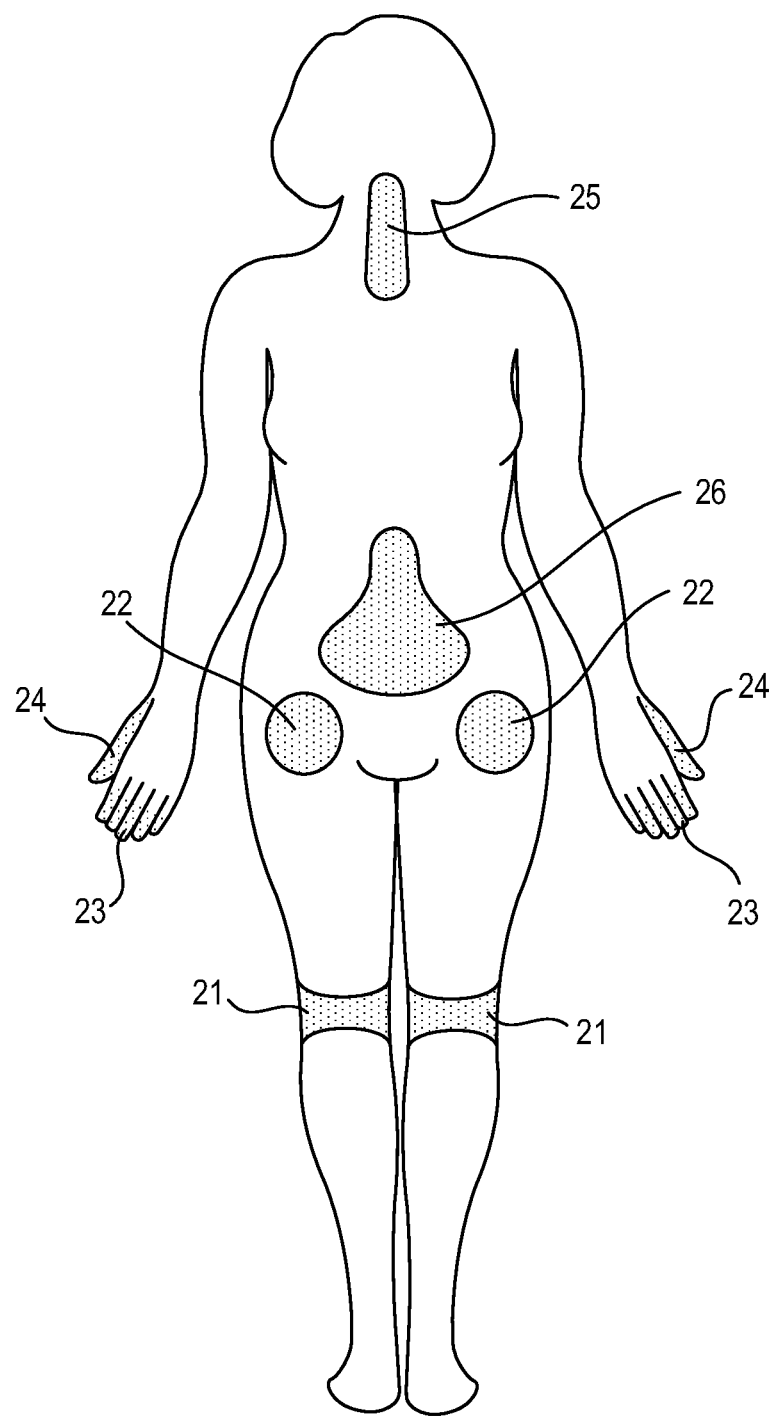
FIG. 1 illustrates a number of common locations within a patient that may be sites at which surgery takes place and locations at which a drug depot containing bupivacaine and clonidine can locally be administered thereto and used to treat post-operative pain.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Unless otherwise specified or apparent from context, where this specification and the set of claims that follows refer to clonidine, the inventors are also referring to pharmaceutically acceptable salts of clonidine. One commercially available salt of clonidine is the hydrochloride salt. Some examples of other potentially pharmaceutically acceptable salts of active compounds include those salt-forming acids and bases that do not substantially increase the toxicity of the compound. Some examples of suitable salts include salts of alkali metals such as magnesium, potassium and ammonium. Salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. To the extent these salts of clonidine can be created for safe administration to a mammal, they are within the scope of the present invention.

Further, when referring to clonidine the active ingredient may not only be in the salt form, but also in the base form. If it is in the base form, it may be combined with polymers under conditions in which there is not severe polymer degradation.

Similarly, when referring to bupivacaine, unless otherwise specified or apparent from context it is understood that the inventors are also referring to pharmaceutically acceptable salts. Some examples of potentially pharmaceutically acceptable salts include those salt-forming acids and bases that do not substantially increase the toxicity of the compound. Some examples of these salts include salts of alkali metals such as magnesium, potassium and ammonium. Salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. To the extent these salts of bupivacaine can be created for safe administration to a mammal, they are within the scope of the present invention.

Further, the bupivacaine may also be used in a base form. As with clonidine, a polymer with which bupivacaine is combined may form a composition for which there will not be significant degradation when processed.

The methods and compositions described herein are not limited to uses in connection with any specific surgery and include but are not limited to treatment of pain that may be associated with arthroscopic surgery, laparoscopic surgery, open back surgery, oral surgery, etc.

A "drug depot" is the composition in which the clonidine and bupivacaine or their pharmaceutically acceptable salts are administered to the body. These active ingredients may be combined in the same or different drug depots. Thus, a drug depot may comprise a physical structure to facilitate implantation and retention in a desired site (e.g., a disc space, a spinal canal, a tissue of the patient, particularly at or near a site of surgery, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified, a "drug" formulation may include more than one therapeutic agent, wherein exemplary combinations of therapeutic agents include a combination of two or more drugs.

The drug provides a concentration gradient of the therapeutic agent for delivery to the site. In various embodiments, the drug depot provides an optimal drug concentration gradient of the therapeutic agent at a distance of up to about 0.01 cm to about 5 cm from the implant site, and comprises clonidine or a pharmaceutically acceptable salt thereof and bupivacaine or a pharmaceutically acceptable salt thereof.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces. As persons of ordinary skill are aware a sustain release (or "sustained release") formulation is a formulation that permits the active ingredient to become accessible over a period of time, e.g. hours or days at a desired rate. By contrast, an immediate release formulation is accessible immediately or essentially immediately. The two types of formulations may be used in conjunction. For example, a bolus or immediate release formulation of bupivacaine or its pharmaceutically acceptable salt and clonidine or its pharmaceutically acceptable salt may be placed at or near the surgery site and a sustain release formulation may also be placed at or near the same site. Thus, even after the bolus becomes completely accessible, the sustain release formulation would continue to provide the active ingredient for the intended tissue.

The bupivacaine or its pharmaceutically acceptable salt and clonidine or its pharmaceutically acceptable salt may be administered with a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocurine, vecuronium, or combinations thereof.

The drug depot may also comprise other therapeutic agents or active ingredients in addition to the bupivacaine or its pharmaceutically acceptable salt and clonidine or its pharmaceutically acceptable salt. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-IRa), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, antioxidants, such as dithiocarbamate, and other compounds, such as, for example, sulfasalazine.

Additional specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine[2-hydroxy-5-[-4-[C2-pyridinylamino)sulfonyl]azo]benzoic acid], indomethacin, ibuprofen, naproxen, ketorolac, tolmetin, or pharmaceutically acceptable salts thereof and diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine amitriptyline, carbamazepine, gabapentin, pregabalin, or a combination thereof.

The clonidine and bupivacaine may also be administered with non-active ingredients. These non-active ingredients may have multi-functional purposes including the carrying, stabilizing and controlling the release of the therapeutic agent (s). The sustained release process, for example, may be by a solution-diffusion mechanism or it may be governed by an erosion-sustained process. Typically, the depot will be a solid or semi-solid formulation comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In various embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these drug depots may need to be removed after a certain period of time.

In some instance, it may be desirable to avoid having to remove the drug depot after use. In those instances, the depot may comprise a biodegradable material. There are numerous materials available for this purpose that has the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a bioerodible, a bioabsorbable, and/or a biodegradable biopolymer that may provide immediate release, or sustained release of the bupivacaine and clonidine. Examples of suitable sustain release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters (POE), polyaspirins, polyphosphazenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

The polymers may be processed by either solvent or heat as long as the formulation containing drug and/or excipient is well mixed within the dosage form. Excipients may be added to the formulation to help with the drug release properties and/or to help with the mechanical properties of the polymer. For example, adding mPEG to PLGA has a plasticizing effect on the polymer, but it also affects the diffusion properties of the drug from the polymer.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt. %, and more typically within the range of 0-30 wt. %. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbonlike) and the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 mm to about 2 mm. In various embodiments, the drug depot may have a layer thickness of from about 0.005 mm to 1.0 mm, such as, for example, from 0.05 to 0.75 mm.

In various embodiments, when the drug depot comprises a ribbon-like fiber, it may be placed at the incision site before the site is closed. The ribbon-like strips may for example be made of thermosplastic materials. Additionally, specific materials that may be advantageous for use as ribbon-like strips include but are not limited to the compounds identified above as sustain release biopolymers. The ribbon-like strip may be formed by mixing the bupivacaine and the clonidine with a polymer and then extruding it.

In various embodiments, the depot may comprise of a biodegradable polyorthoester. The mechanism of the degradation process of the polyorthoester can be hydrolytical or enzymatical in nature, or both. In various embodiments, the degradation can occur either at the surface (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

In various embodiments, the drug depot can be designed to cause an initial burst dose of therapeutic agent within the first twenty-four hours after implantation. "Initial burst" or "burst effect" or "bolus dose" refers to the release of therapeutic agent from the depot during the first twenty-four to forty-eight hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid this initial burst effect.

In various embodiments, when the depot is a gel, the gel has a pre-dosed viscosity in the range of about 1 to about 2000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising bupivacaine and clonidine that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times -10^2$ to about $2 \times 10^6$ dynes/cm$^2$, or $1 \times 10^5$ to about $7 \times 10^5$ dynes/cm$^2$, or $2 \times 105$ to about $5 \times 10^5$ dyne/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone). In other various embodiments, the gel will not harden upon tissue contact after being injected to the tissue site.

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, chain transfer or chain capping agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer, tends to coagulate or solidify more quickly than a polymeric composition that includes a low-molecular weight polymer. Polymeric gel formulations that include high molecular weight polymers, also tend to have a higher solution viscosity than polymeric gels that includes low-molecular weight polymers.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by spraying, brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly(methoxyethylmethacrylate), poly-(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

A gel with a higher viscosity may be desirable for certain applications, for example, a gel having a putty-like consistency may be more preferable for bone regeneration applications. In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof. In some embodiments, the gel is biodegradable.

In various embodiments, rather than directly admixing the therapeutic agents into the gel, bupivacaine and clonidine loaded polymer microspheres may be dispersed within the gel. In one embodiment, the microspheres provide for a sustained release of both bupivacaine and clonidine. The bupivacaine and clonidine may occupy the same or different microspheres. In yet another embodiment, a biodegradable gel prevents the microspheres from releasing the bupivacaine and clonidine; the microspheres thus do not release the bupivacaine and clonidine until the microspheres themselves have been released from the gel. For example, a gel may be deployed around a target tissue site (e.g., a nerve root), thus allowing the drug loaded microspheres to deliver drug directly to the point of interest.

Microspheres, much like a fluid, may disperse relatively quickly, depending upon the surrounding tissue type, and hence disperse the bupivacaine and clonidine. In some situations, this may be desirable; in others, it may be more desirable to keep the bupivacaine and clonidine tightly constrained to a well-defined target site. The present invention also contemplates the use of adherent gels to so constrain dispersal of the therapeutic agent. These gels may be deployed, for example, in a disc space, in a spinal canal, or in surrounding tissue.

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high nonferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The preferred dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 mm to about 1.655 mm. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, iodine, tantalum, tungsten, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy that is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kit

In various embodiments, a kit is provided that may include additional parts along with the drug depot and/or medical device combined together to be used to implant the drug depot (e.g., ribbon-like fibers). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility.

Administration

In various embodiments, the drug depot containing the active ingredient(s) may be parenterally administered. In addition to including administration that is intravenous, intramuscular, through continuous or intermittent infusion, intraperitoneal, intrasternal, subcutaneous, intra-operatively, intrathecally, intradiskally, peridiskally, epidurally, perispinally, intra-articularly or a combination thereof, parenteral administration also includes an infusion pump that administers a pharmaceutical composition through a catheter near the target site, an implantable mini-pump that can be inserted at or near the target site, and/or an implantable controlled release device or sustained release delivery system that can release a certain amount of the composition per hour or in intermittent bolus doses.

One example of a suitable pump for use is the SynchroMed® (Medtronic, Minneapolis, Minn.) pump. The pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals.

Potential drug delivery devices suitable for adaptation for the methods described herein include but are not limited to those described, for example, in U.S. Pat. No. 6,551,290 (assigned to Medtronic, the entire disclosure of which is herein incorporated by reference), which describes a medical catheter for target specific drug delivery; U.S. Pat. No. 6,571, 125 (assigned to Medtronic, the entire disclosure of which is herein incorporated by reference), which describes an implantable medical device for controllably releasing a biologically active agent; U.S. Pat. No. 6,594,880 (assigned to Medtronic, the entire disclosure of which is herein incorporated by reference), which describes an interparenchymal infusion catheter system for delivering therapeutic agents to selected sites in an organism; and U.S. Pat. No. 5,752,390 (assigned to Medtronic, the entire disclosure of which is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, lightweight devices for delivering liquid medication, implantable micro-miniature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods.

In various embodiments, a method for delivering a therapeutic agent into a surgery site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered (e.g., brushed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. By way of example, the administration of the effective dosages of bupivacaine and clonidine may be used to prevent, treat or relieve the symptoms of pain incidental to surgery.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots, gels or depot dispersed in the gel having a quantity of therapeutic agent that can be deposited at or near the target site as needed for treatment of pain, inflammation or other disease or condition. In various embodiments the formulations are preservative free.

FIG. 1 illustrates a number of common locations within a patient that may be sites at which surgery can take place. It will be recognized that the locations illustrated in FIG. 1 are merely exemplary of the many different locations within a patient that may be at which surgery can take place. For example, surgery may be required at a patient's knees 21, hips 22, fingers 23, thumbs 24, neck 25, and spine 26. Thus, during or following these surgeries, the patient may be subject to pain and require pain management medication.

The term "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

Figure 2:
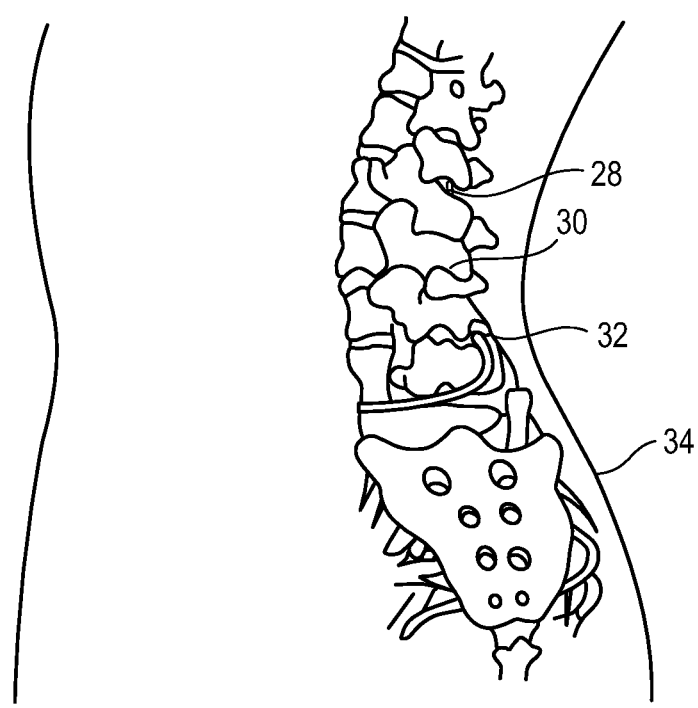
FIG. 2 illustrates a schematic dorsal view of the spine and sites where the drug depot containing bupivacaine and clonidine can locally be administered thereto.

One exemplary embodiment where the depot is suitable for use in post-operative pain as illustrated in FIG. 2. Schematically shown in FIG. 2 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

In some embodiments, it is preferable to co-administer bupivacaine and clonidine with an antagonist to counteract undesirable effects, for example the blood pressure decrease that can be caused by clonidine. Exemplary antagonists include but are not limited to phentolamine, yohimbine, tolazoline or piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

The bupivacaine and clonidine-based formulation described herein may be used as medicaments in the form of pharmaceutical preparations. The preparations may be formed with a suitable pharmaceutical carrier that may be solid, semi-solid or liquid, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Another embodiment provides a method for treating a mammal suffering from pain associated with surgery, said method comprising administering a therapeutically effective amount of bupivacaine and clonidine at a target site beneath the skin to relax muscle at or near the target site. The bupivacaine and clonidine may for example be administered locally to the target tissue site as a drug depot. The term "locally" refers to a proximity to the site of interest such that when the drug is released, an effective amount of the bupivacaine and clonidine will reach the site.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "release rate profile" refers to the percentage of active ingredient that is released over fixed units of time, e.g., mcg/hr, mcg/day, 10% per day for ten days, etc. As persons of ordinary skill know, a release rate profile may be but need not be linear. By way of a non-limiting example, the drug depot may be a ribbon-like fiber that releases the bupivacaine and clonidine over a period of time.

In some embodiments, the therapeutically effective dosage amount and the release rate profile are sufficient to treat the post-operative pain or disease or condition for a period of 3-12 days; in other embodiments the release rate profile is sufficient to treat for a period of 7-10 days.

In some embodiments, the bupivacaine and clonidine are encapsulated in a plurality of depots comprising microparticles, microspheres, microcapsules, and/or microfibers. The active ingredients may be combined and then encapsulated or first encapsulated and then combined.

In some embodiments there is a composition useful for the treatment of post-operative pain comprising an effective amount of bupivacaine and clonidine that is capable of being administered to a post-operative surgery site.

In some embodiments, the dosage of clonidine is from approximately 0.0005 to approximately 100 µg/kg/day. Other dosages of clonidine can include from approximately 0.0005 to approximately 95 µg/kg/day; approximately 0.0005 to approximately 90 µg/kg/day; approximately 0.0005 to approximately 85 µg/kg/day; approximately 0.0005 to approximately 80 µg/kg/day; approximately 0.0005 to approximately 75 µg/kg/day; approximately 0.001 to approximately 70 µg/kg/day; approximately 0.001 to approximately 65 µg/kg/day; approximately 0.001 to approximately 60 µg/kg/day; approximately 0.001 to approximately 55 µg/kg/day; approximately 0.001 to approximately 50 µg/kg/day; approximately 0.001 to approximately 45 µg/kg/day; approximately 0.001 to approximately 40 µg/kg/day; approximately 0.001 to approximately 35 µg/kg/day; approximately 0.0025 to approximately 30 µg/kg/day; approximately 0.0025 to approximately 25 µg/kg/day; approximately 0.0025 to approximately 20 µg/kg/day; and approximately 0.0025 to approximately 15 µg/kg/day. In another embodiment, the dosage of clonidine is from approximately 0.005 to approximately 15 µg/kg/day. In another embodiment, the dosage of clonidine is from approximately 0.005 to approximately 10 µg/kg/day. In another embodiment, the dosage of clonidine is from approximately 0.005 to approximately 5 µg/kg/day. In another embodiment, the dosage of clonidine is from approximately 0.005 to approximately 20 µg/kg/day.

In some embodiments it is desirable to use a sufficient amount of clonidine to be detected in the blood at least 1 microgram per kilogram of bodyweight, and preferably in an amount of 2-8 micrograms per kilogram, and even more preferably 3-6 micrograms per kilogram of bodyweight. Further, in some embodiments, it is desirable to administer a sufficient amount of clonidine in a single sustained release formulation to sustain this level for 3-12 days or 7-10 days.

In various embodiments, the drug depot releases about 1 mg to 30 mg/day of bupivacaine for 1 to 10 days or 1 day to 6 months. In some embodiments it releases 20 to 360 mg/day or 40 to 120 mg/day or 80 to 180 mg/day or 120 to 240 mg/day or 160 to 300 mg/day or 200 to 360 mg/day or bupivacaine. This dose is often much lower than the dose used to provide nerve block in surgery.

In various embodiments, where the target tissue site comprises blood vessels, a vasoconstrictor may be employed either in or in connection with the drug depot. When the vasoconstrictor is released, it lengthens the duration of an anesthetic response and reduces the systemic uptake of an anesthetic agent, such as bupivacaine. Exemplary vasoconstrictors include but are not limited to catecholamines e.g., epinephrine, norepinephrine and dopamine, as well as, e.g., metaraminol, phenylephrine, methoxamine, mephentermine, methysergide, ergotamine, ergotoxine, dihydroergotamine, sumatriptan and analogs, and alpha-1 and alpha-2 adrenergic agonists, such as, e.g., guanfacine, guanabenz and dopa (i.e., dihydroxyphenylalanine), methyldopa, ephedrine, amphetamine, methamphetamine, methylphenidate, ethylnorepinephrine ritalin, pemoline and other sympathomimetic agents, including active metabolites, derivatives and mixtures of any of the foregoing.

In some embodiments, the bupivacaine and clonidine are administered parenterally, e.g., by injection. In some embodiments, the injection is intrathecal, which refers to an injection into the spinal canal (intrathecal space surrounding the spinal cord). An injection may also be into a muscle or other tissue. In other embodiments, the clonidine and bupivacaine is administered by placement into an open patient cavity during surgery itself.

In some embodiments, the present invention provides a medicinal composition comprising: (a) a therapeutically effective amount of bupivacaine or a pharmaceutically acceptable salt thereof; and (b) a therapeutically effective amount of clonidine or a pharmaceutically acceptable salt thereof. The medicinal compound made further comprise a polymer, e.g., poly(lactic-co-glycolic acid), which is also known as poly(lactide-co-glycolide).

In various embodiments, the molecular weight of the polymer can be a wide range of values. The average molecular weight of the polymer can be from about 1,000 to about 10,000,000; or about 1,000 to about 1,000,000; or about 5,000 to about 500,000; or about 10,000 to about 100,000; or about 20,000 to 50,000.

As persons of ordinary skill in the art are aware, an implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

In various embodiments, the drug depot comprises poly (lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof.

A formulation of the active ingredients of bupivacaine and clonidine, in combination with a suitable polymer (e.g., PLG) may be malleable and can be extruded into ribbon-like dosage form. In some embodiments, the formulation is implantable into a surgical site at the time of surgery. The active ingredients may then be released from the depot via diffusion in a sustained fashion over a period of time, e.g., 3-12 days, 5-10 days or 7-10 days post surgery in order to provide pain control.

In some embodiments, the present invention is directed to a method of treating or preventing postoperative pain or inflammation in a patient in need of such treatment, the method comprising administering one or more biodegradable drug depots comprising a therapeutically effective amount of bupivacaine or pharmaceutically acceptable salt thereof and clonidine or pharmaceutically acceptable salt thereof to a target tissue site beneath the skin, wherein the drug depot releases an effective amount of bupivacaine or pharmaceutically acceptable salt thereof and clonidine or pharmaceutically acceptable salt thereof over a period of 3 to 12 days or 5 to 10 days.

In some embodiments of the present invention, the drug depot may release 5%, 10%, 15%, 20%, 25%, 30%, 40%, 50%, 60%, 70%, 80%, 90%, 95%, or 99% of the bupivacaine or pharmaceutically acceptable salt thereof and clonidine or pharmaceutically acceptable salt thereof relative to a total amount of bupivacaine or pharmaceutically acceptable salt thereof and clonidine or pharmaceutically acceptable salt thereof loaded in the drug depot over a period of 3 to 12 days after the drug depot is administered to the target tissue site.

In some embodiments of the present invention, the drug depot releases 5 mg to 60 mg of bupivacaine or pharmaceutically acceptable salt thereof and 10 µg to 100 µg of clonidine or pharmaceutically acceptable salt thereof every 4 to 6 hours to treat postoperative pain or inflammation over a span of 3 to 12 days or 5 to 10 days.

By way of non-limiting example, the target tissue site comprises at least one muscle, ligament, tendon, cartilage, spinal disc, spinal foraminal space near the spinal nerve root, facet or spinal canal. Also by way of example, the pain or inflammation is associated with orthopedic or spine surgery or a combination thereof. By way of further example, the surgery may be arthroscopic surgery, an excision of a mass, hernia repair, spinal fusion, thoracic, cervical, or lumbar surgery, pelvic surgery or a combination thereof.

In some embodiments of the present invention, the bupivacaine or pharmaceutically acceptable salt thereof and clonidine or pharmaceutically acceptable salt thereof is encapsulated in a plurality of depots comprising microparticles, microspheres, microcapsules, and/or microfibers suspended in a gel.

In some embodiments, the drug depot further comprises a radiographic marker adapted to assist in radiographic imaging. The radiographic marker may for example, comprise barium, calcium phosphate, and/or metal beads.

In some embodiments, the present invention provides a method of inhibiting postoperative pain or inflammation in a patient in need of such treatment, the method comprising delivering one or more biodegradable drug depots comprising a therapeutically effective amount of bupivacaine or pharmaceutically acceptable salt thereof and clonidine or pharmaceutically acceptable salt thereof to a target tissue site beneath the skin before, during or after surgery, wherein the drug depot releases an effective amount of bupivacaine or pharmaceutically acceptable salt thereof and clonidine or pharmaceutically acceptable salt thereof over a period of 3 to 12 days or 5 to 10 days.

In some embodiments, the present invention provides a method of inhibiting postoperative pain or inflammation, wherein the drug depot (i) releases 2 mg to 60 mg of bupivacaine or pharmaceutically acceptable salt thereof and 10 µg to 100 µg clonidine or pharmaceutically acceptable salt thereof every 4 to 6 hours to inhibit postoperative pain or inflammation. The drug depot may further comprise at least one additional anti-inflammatory or analgesic agent, at least one anabolic or an anti-catabolic growth factor or combination thereof.

In some embodiments, the present invention provides an implantable drug depot useful for preventing or treating post-operative pain or inflammation in a patient in need of such treatment, the implantable drug depot comprising a therapeutically effective amount of bupivacaine or pharmaceutically acceptable salt thereof and clonidine or pharmaceutically acceptable salt thereof, the depot being implantable at a site beneath the skin to prevent or treat postoperative pain, wherein the drug depot releases an effective amount of bupivacaine or pharmaceutically acceptable salt thereof and clonidine or pharmaceutically acceptable salt thereof over a period of 3 to 12 days or 5 to 10 days.

In some embodiments, the present invention provides an implantable drug depot, wherein the drug depot (i) comprises one or more immediate release layer(s) that releases a bolus dose of bupivacaine or pharmaceutically acceptable salt thereof and clonidine or pharmaceutically acceptable salt thereof at a site beneath the skin and (ii) one or more sustain release layer(s) that releases an effective amount of bupivacaine or pharmaceutically acceptable salt thereof and clonidine or pharmaceutically acceptable salt thereof over a period of 3 to 12 days or 5 to 10 days. By way of example, in the drug depot, the one or more immediate release layer(s) may comprise poly(lactide-co-glycolide) (PLGA) and the one or more sustain release layer(s) may comprise polylactide (PLA).

In some embodiments, the clonidine is first compounded with a polymer to make a first component of the drug depot. In this first component, the clonidine may for example, comprise 2.5% to 10% by weight. The bupivacaine may separately be compounded with a polymer to make a second component of the drug depot. In this second component, the bupivacaine may for example comprises 50%-70% by weight. In some embodiments, the percentage of clonidine to bupivacaine is between about 1:30, 1:25, 1:20, 1:15, 1:12.5, 1:11, 1:10, 1:9, 1:8, 1:7, 1:6, 1:5, 1:4, 1:3, 1:2, or 1:1. The bupivacaine and clonidine may also be formulated together a two active ingredients with one polymer. Thus, a combination product comprising clonidine and bupivacaine may by way of example be formed by combining these active ingredients with a polymer as part of one formulation to generate a combination drug product. By way of another example, each active formulation is separately developed for co-administration to a site, e.g., a surgical wound site. The data in Table 1 and Table 2 are examples of formulation that may be used in this latter coadministration. (See also FIGS. 3-6).

In some embodiments, the amount of bupivacaine is between 2 mg/day to 1800 mg/day, and the amount of clonidine is between 40 and 600 µg/day. In some embodiments, the amount of bupivacaine is between 10 and 1500 mg/day, and the amount of clonidine is between 200 and 400 µg/day. The release of each compound may be for at least three, at least four at least five, at least six, at least seven or at least eight days in the recited ranges.

In various embodiments, the drug particle size is from about 5 to 30 micrometers, however, in various embodiments ranges from about 1 micron to 250 microns may be used.

In some embodiments, there is another method of making an implantable drug depot. In this method, one combines a biocompatible polymer and a therapeutically effective amount of bupivacaine or pharmaceutically acceptable salt thereof and clonidine or pharmaceutically acceptable salt thereof and forms the implantable drug depot from the combination.

Processing

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: bupivacaine and clonidine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: bupivacaine and clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, bupivacaine and clonidine may undergo substantial degradation under ordinary thermoplastic processing conditions. Hence, processing is preferably performed under modified conditions, which prevent the substantial degradation of the therapeutic agent (s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the bupivacaine and clonidine containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., bupivacaine and clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of bupivacaine and clonidine, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where a water-soluble therapeutic agent such as bupivicaine and clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape.

EXAMPLES

Example 1

Varying Ranges of Total % Drug Loading

Materials:
Poly(d,l lactide-co-glycolide) having a 50:50 lactide to glycolide molar ratio (PLGA50501A), an intrinsic viscosity of 0.12 and acid end capped polymer chain ends was purchased from Lakeshore Biomaterials (Birmingham, Ala.). Bupivacaine Base was purchased from Orgamol (Switzerland). Clonidine HCl and was purchased from Spectrum Chemicals (Gardena, Calif.). Methoxy polyethylene glycol (mPEG) having an average molecular weight of 550 was purchased from Sigma-Aldrich. Methanol was also purchased from Sigma-Aldrich.

Methods:
Preparation of Spray Dried Clonidine HCl: Clonidine HCl was dissolved in methanol to yield a 12% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mmHg vacuum.

Figure 9A:
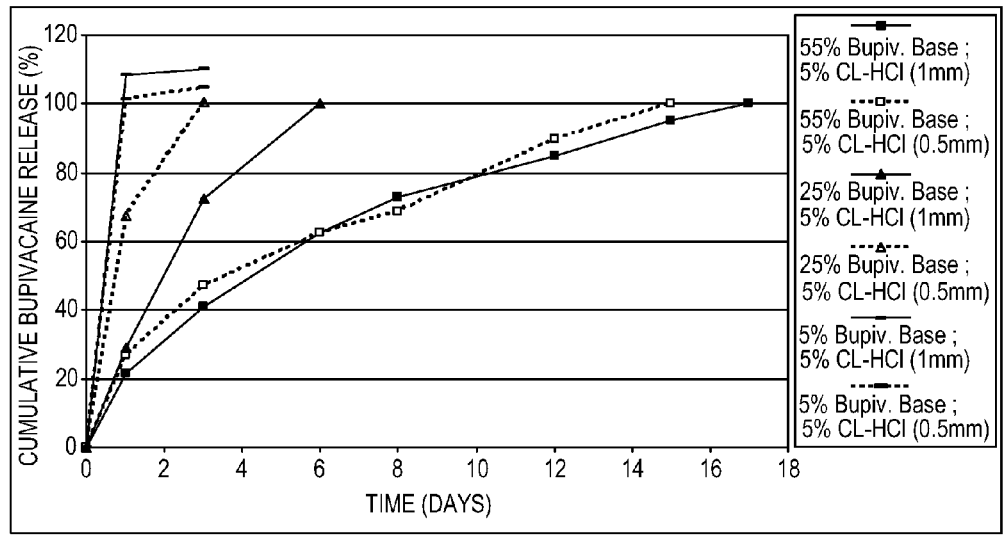
FIGS. 9A-9B are in vitro graphic representations of studies of the percentage cumulative release of sterilized bupivacaine and clonidine in the same formulation. Here the wt % clonidine was kept constant and the wt % drug depot load for the bupivacaine changed.
Figure 9B:
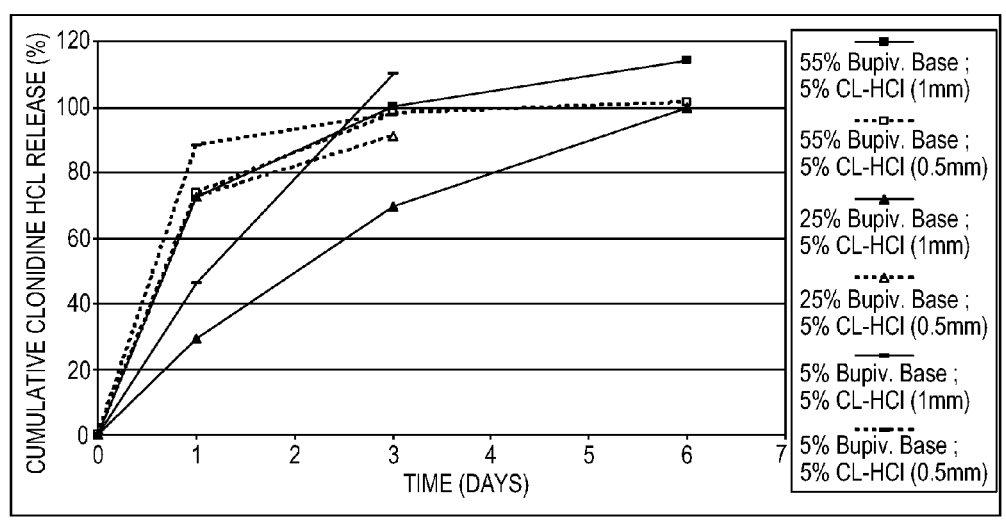

Preparation of Melt Extruded Rods: Three formulations were prepared for melt extrusion. All formulations contained PLGA50501A ground into powder using a Retsch (Retsch GmbH, Germany) rotor mill with an 80 micrometer sieve filter. The first such formulation contained 30% (w/w) ground PLGA50501A, 5% (w/w) spray dried clonidine HCl, 55% (w/w) bupivacaine base and 10% (w/w) mPEG (60% drug). The second formulation contained 60% (w/w) ground PLGA50501A, 5% (w/w) spray dried clonidine HCl, 25% (w/w) bupivacaine base and 10% (w/w) mPEG (30% drug). The third formulation contained 80% (w/w) ground PLGA50501A, 5% (w/w) spray dried clonidine HCl, 5% (w/w) bupivacaine base, and 10% (w/w) mPEG (10% drug). The cumulative bupivacaine release % for the formulations are shown in FIG. 9A and the cumulative clonidine release % for the formulations are shown in FIG. 9B. All formulations were dry mixed with a spatula prior to being feed into a Haake Mini-Lab twin screw extruder (Thermo Fischer Scientific, Waltham, Mass.). The extruder settings were as follows: 70° C. and 30 RPM for the 30% & 10% drug formulations, and 85° C. and 30 RPM for the 60% drug formulation. All formulations were extruded out of a 1.5 mm diameter die.

Ribbon Preparation: Extruded formulations were pressed into sheets of a desired thickness using a Carver Laboratory Heat Press (Carver, Inc., Wabash, Ind.) set at 50° C. The sheets were cut by razor blades to form ribbons of the desired dimensions. The dimensions of each formulation are 9 mm×3 mm×1 mm (L×W×H).

In-Vitro Drug Elution Testing: Each ribbon formulation was tested in triplicate and placed in 20 mL scintillation vials for drug elution testing. The ribbon formulations were incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified at 260 nm and 226 nm for bupivacaine and clonidine respectively by Molecular Devices SpectraMax M2 (Sunnyvale, Calif.) plate reader.

FIGS. 9A-9B are in vitro graphic representations of studies of the percentage cumulative release of sterilized bupivacaine and clonidine in the same formulation. FIG. 9A illustrates cumulative bupivacaine release % for the formulations. Here the wt % clonidine was kept constant and the wt % drug depot load for the bupivacaine changed. In general, clonidine wt % did no effect release of the bupivacaine. The formulation with drug loads of clonidine 5% and bupivacaine 5% had over 100% release of the bupivacaine within the first two days (an initial burst effect). These formulations had very low drug loads. The formulation with drug loads of clonidine 5% and bupivacaine 25% had over 100% release of the bupivacaine within the first two days. The formulations that had a low thickness (0.5 mm) had a faster release of the bupivacaine than the formulations with the same composition but higher thickness (1 mm). The formulation with drug loads of clonidine 5% and bupivacaine 25% (1 mm thickness) had over 100% release within six days. The formulation with drug loads of clonidine 5% and bupivacaine 55% (1 mm thickness) had over 100% release within 17 days. The formulation with drug loads of clonidine 5% and bupivacaine 55% (0.5 mm thickness) had over 100% release within 15 days. In general, increasing the drug load increased the duration of action and increasing the thickness of the depot prolonged the release. These formulations can be used to prevent, treat or inhibit POP.

FIG. 9B illustrates cumulative clonidine release % for the formulations. Here the wt % clonidine was kept constant and the wt % drug depot load for the bupivacaine changed. In general, clonidine wt % did no effect release of the bupivacaine. All formulations released 100% of the clonidine load within one to six days. In general, increasing the thickness of the depot prolonged the drug release. Keeping the clonidine: bupivacaine ratio between 1:11, 1:5, and 1:1 did not significantly affect drug release of the bupivacaine.

Example 2

Varying Bupivacaine Base:Clonidine HCl Ratio

Materials:
Poly(d,l lactide-co-glycolide) having a 50:50 lactide to glycolide molar ratio (PLGA50501A), an intrinsic viscosity of 0.12 and acid end capped polymer chain ends was purchased from Lakeshore Biomaterials (Birmingham, Ala.). Bupivacaine Base was purchased from Orgamol (Switzerland). Clonidine HCl and was purchased from Spectrum Chemicals (Gardena, Calif.). Methoxy polyethylene glycol (mPEG) having an average molecular weight of 550 was purchased from Sigma-Aldrich. Methanol was also purchased from Sigma-Aldrich.

Methods:
Preparation of Spray Dried Clonidine HCl: Clonidine HCl was dissolved in methanol to yield a 12% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mmHg vacuum.

Figure 10A:
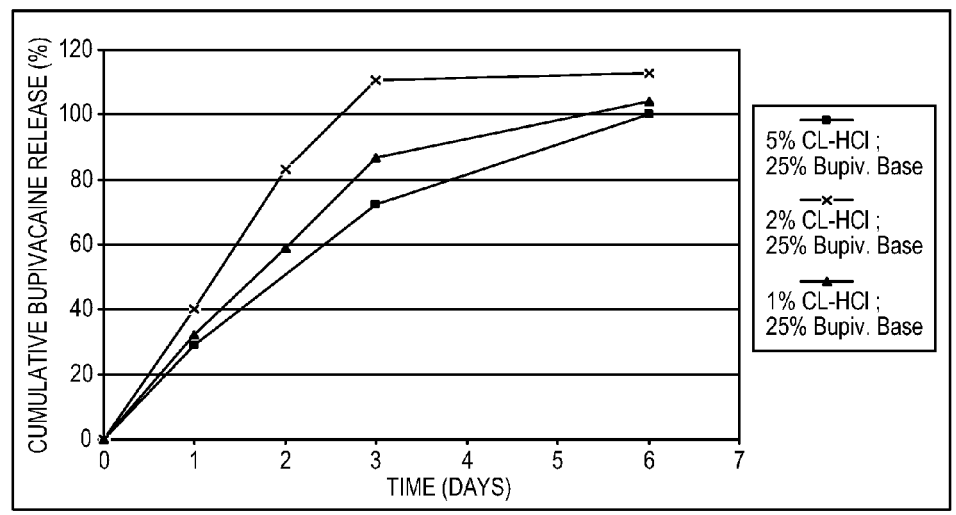
FIGS. 10A-10B are in vitro graphic representations of studies of the percentage cumulative release of sterilized bupivacaine and clonidine in the same formulation. Here the wt % bupivacaine was kept constant and the wt % drug depot load for the clonidine changed.
Figure 10:
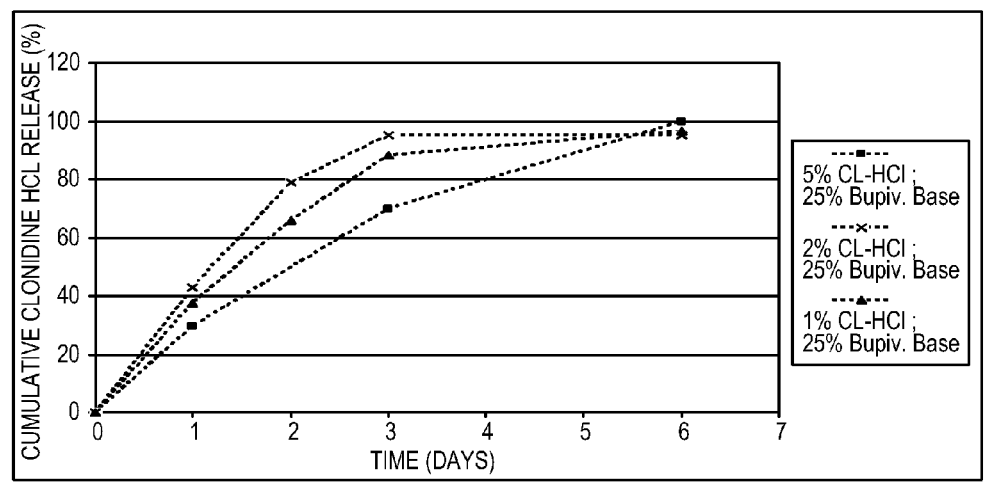

Preparation of Melt Extruded Rods: Three formulations were prepared for melt extrusion. All formulations contained PLGA50501A ground into powder using a Retsch (Retsch GmbH, Germany) rotor mill with an 80 micrometer sieve filter. The first such formulation contained 80% (w/w) ground PLGA50501A, 5% (w/w) spray dried clonidine HCl, 25% (w/w) bupivacaine base and 10% (w/w) mPEG (1:5 ratio). The second formulation contained 80% (w/w) ground PLGA50501A, 2% (w/w) spray dried clonidine HCl, 25% (w/w) bupivacaine base and 10% (w/w) mPEG (1:12.5 ratio). The third formulation contained 80% (w/w) ground PLGA50501A, 1% (w/w) spray dried clonidine HCl, 25% (w/w) bupivacaine base, and 10% (w/w) mPEG (1:25 ratio). The in vitro elution profiles for these formulations are shown in FIGS. 10A and 10B. All formulations were dry mixed with a spatula prior to being fed into a Haake Mini-Lab twin screw extruder (Thermo Fischer Scientific, Waltham, Mass.). The extruder settings were set at 70° C. and 30 RPM and extruded out of a 1.5 mm diameter die.

Ribbon Preparation: Extruded formulations were pressed into sheets of a desired thickness using a Carver Laboratory Heat Press (Carver, Inc., Wabash, Ind.) set at 50° C. The sheets were cut by razor blades to form ribbons of the desired dimensions. The dimensions of each formulation are 9 mm×3 mm×1 mm (L×W×H).

In-Vitro Drug Elution Testing: Each ribbon formulation was tested in triplicate and placed in 20 mL scintillation vials for drug elution testing. The ribbon formulations were incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified at 260 nm and 226 nm for bupivacaine and clonidine respectively by Molecular Devices SpectraMax M2 (Sunnyvale, Calif.) plate reader.

FIG. 10A is an in vitro graphic representation of studies of the percentage cumulative release of sterilized bupivacaine and clonidine in the same formulation. Here the wt % bupivacaine was kept constant and the wt % drug depot load for the clonidine changed. All formulations released 100% of the bupivacaine load within 6 days. The release profiles were similar. Thus keeping the clonidine:bupivacaine ratio between 1:5, 1:12.5, and 1:25 did not significantly affect drug release of the bupivacaine.

FIG. 10B is an in vitro graphic representation of studies of the percentage cumulative release of sterilized bupivacaine and clonidine in the same formulation. Here the wt % bupivacaine was kept constant and the wt % drug depot load for the clonidine changed. All formulations released about 100% of the clonidine load within 6 days. The release profiles were similar. Thus keeping the clonidine:bupivacaine ratio between 1:5, 1:12.5, and 1:25 did not significantly affect drug release of the clonidine.

Example 3

Layered Ribbon Formulation

Materials:
Poly(d,l lactide-co-glycolide) having a 50:50 lactide to glycolide molar ratio (PLGA50501A), an intrinsic viscosity of 0.12 and acid end capped polymer chain ends was purchased from Lakeshore Biomaterials (Birmingham, Ala.). Bupivacaine base was purchased from Orgamol (Switzerland). Clonidine HCl and was purchased from Spectrum Chemicals (Gardena, Calif.). Methoxy polyethylene glycol (mPEG) having an average molecular weight of 550 was purchased from Sigma-Aldrich. Methanol was also purchased from Sigma-Aldrich.

Methods:
Preparation of Spray Dried Clonidine HCl: Clonidine HCl was dissolved in methanol to yield a 12% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mmHg vacuum.

Preparation of Melt Extruded Rods: Four formulations were prepared for melt extrusion. All formulations contained PLGA50501A ground into powder using a Retsch (Retsch GmbH, Germany) rotor mill with an 80 micrometer sieve filter. The first such formulation contained 85% (w/w) ground PLGA50501A, 5% (w/w) spray dried clonidine HCl, and 10% (w/w) mPEG (5% clonidine HCl). The second formulation contained 35% (w/w) ground PLGA50501A, 55% (w/w) bupivacaine base and 10% (w/w) mPEG (55% bupivacaine base). The third formulation contained 65% (w/w) ground PLGA50501A, 25% (w/w) bupivacaine base, and 10% (w/w) mPEG (25% bupivacaine base). The fourth formulation contained 85% (w/w) ground PLGA50501A, 5% (w/w) bupivacaine base, and 10% (w/w) mPEG (5% bupivacaine base).

Figure 11A:
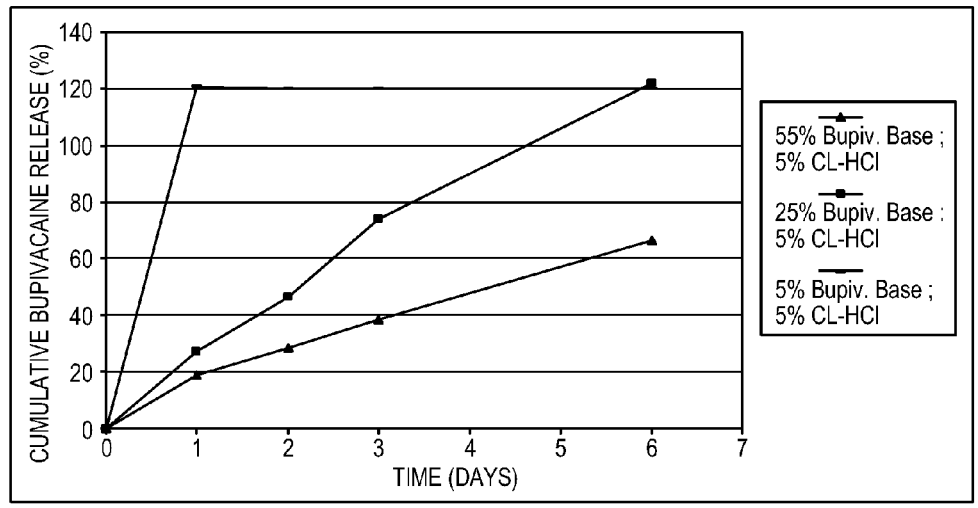
FIGS. 11A-11B are in vitro graphic representations of studies of the percentage cumulative release of sterilized bupivacaine and clonidine in the same formulation. Here the wt % clonidine was kept constant and the wt % drug depot load for the bupivacaine changed.
Figure 11B:
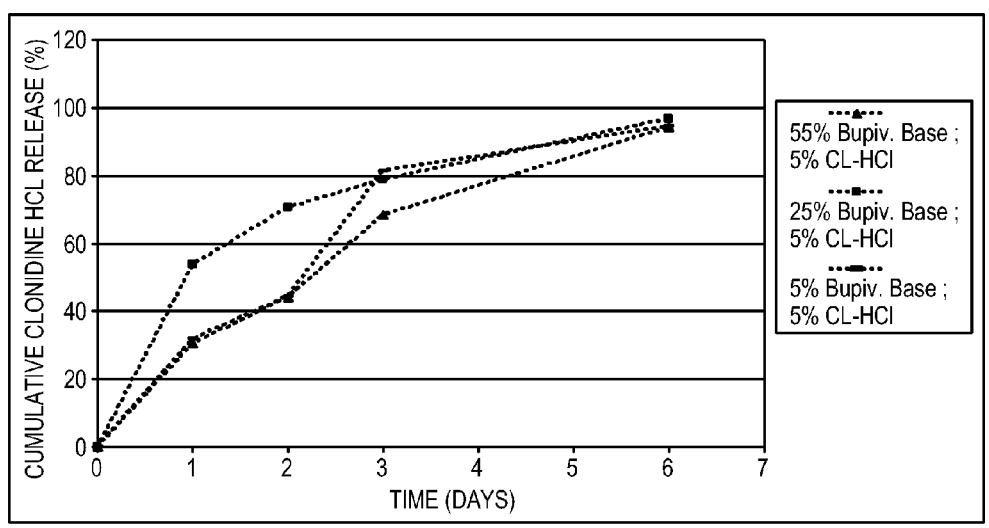

FIGS. 11A-11B are in vitro graphic representations of studies of the percentage cumulative release of sterilized bupivacaine and clonidine in the same formulation for the formulations in Example 3. Here the wt % clonidine was kept constant and the wt % drug depot load for the bupivacaine changed.

All formulations were dry mixed with a spatula prior to being feed into a Haake Mini-Lab twin screw extruder (Thermo Fischer Scientific, Waltham, Mass.). The extruder settings were as follows: 70° C. and 30 RPM for the 25% bupivacaine, 5% bupivacaine, and 5% clonidine formulations, and 85° C. and 30 RPM for the 55% bupivacaine formulation. All formulations were extruded out of a 1.5 mm diameter die.

Ribbon Preparation: Extruded formulations were pressed into sheets of a desired thickness using a Carver Laboratory Heat Press (Carver, Inc., Wabash, Ind.) set at 50° C. The sheets were cut by razor blades to form ribbons of the desired dimensions. The dimensions of each formulation are (L×W×H): 9 mm×3 mm×1 mm for all three bupivacaine formulations and 9 mm×3 mm×0.25 mm for the clonidine formulation. The layered ribbons were prepared by placing one clonidine ribbon directly on top of each of the three bupivacaine formulations. Gentle hand pressure is needed to connect the two ribbons in place.

5%. The formulation having 55% bupivacaine load had the longest release with over 60% of the bupivacaine being released in 6 days. The drug depot with 5% clonidine and 5% bupivacaine (1:1 ratio) released all of the bupivacaine within 1 day. The drug depot with 5% clonidine and 25% bupivacaine (1:5 ratio) released bupivacaine consistently over 6 days. Increasing the bupivacaine drug load prolonged release.

FIG. 11B is an in vitro graphic representation of studies of the percentage cumulative release of sterilized bupivacaine and clonidine in the same formulation. Here the wt % clonidine was kept constant and the wt % drug depot load for the bupivacaine changed. All formulations released about 100% of the clonidine load within 6 days. The release profiles were similar. Thus keeping the clonidine:bupivacaine ratio between 1:1, 1:5, and 1:11, did not significantly affect drug release of the clonidine.

Example 4

Elution Profile and In Vivo Data

Certain formulations of bupivacaine and clonidine were tested in Brennan rats to determine their in vitro elution and in vivo performance. The results are summarized below in Table 1:

TABLE 1

| | | Bupivacaine | | | | |
|---|---|---|---|---|---|---|
| Formulation Number | Polymer | Active Wt. % of Bupivacaine | Excipient | Handling Property | In vitro elution profile | In vivo data |
| bupivacaine 1 (elution shown in FIG. 3) | 30% PLGA 50501 A | 60% (bupivacaine HCl) | 10% mPEG | Sticky, malleable | Day 1 release of 47%. By day 7, 100% released | No statistical reduction in hyperalgesia |
| bupivacaine 2 (elution shown in FIGS. 3 and 4) | 30% PLGA 50501 A | 60% (bupivacaine base) | 10% mPEG | Sticky, malleable | Day 1 release of 20%. By day 9, 70% released | Statistically significant reduction in mechanical hyperalgesia on day 2. |
| bupivacaine 3 | PLA-C12 gel | 30% (bupivacaine base) | | Injectable | Day 1 burst release of 30%, By day 10, 70% of the drug eluted. | Not tested |

In-Vitro Drug Elution Testing: Each of the three layered ribbon formulations were tested in triplicate and placed in 20 mL scintillation vials for drug elution testing. The ribbon formulations were incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified at 260 nm and 226 nm for bupivacaine and clonidine respectively by Molecular Devices SpectraMax M2 (Sunnyvale, Calif.) plate reader.

FIG. 11A is an in vitro graphic representation of studies of the percentage cumulative release of sterilized bupivacaine and clonidine in the same formulation. Here the wt % of clonidine was kept constant and the wt % drug depot load for the bupivacaine changed. The formulations were designed in a bi-layered ribbon. The clonidine load was kept constant at Throughout the examples, the following inherent viscosity (IV) designations for the polymer in Table A apply.

TABLE A

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |

TABLE A-continued

| IV Target Designator | IV Range |
|---|---|
| 8 | 0.70-0.90 |
| 9 | 0.80-1.0 |

The final letter within the code of the polymer is the end group designator. For examples "E" refers to an ester end group, while "A" refers to an acid end group.

By way of example, 100 DL 7E is a polymer that has an inherent viscosity of 0.60-0.80 dL/g. It contains 100% poly (DL-lactide) that has ester end groups. It is available from Lakeshore Biomaterials, Birmingham, Ala.

the administration of bupivacaine formulation 2, where as there was not statistical effect with bupivacaine formulation 1.

For bupivacaine formulation 3, the degradation of the polymer took at least a couple of months.

Figure 7:
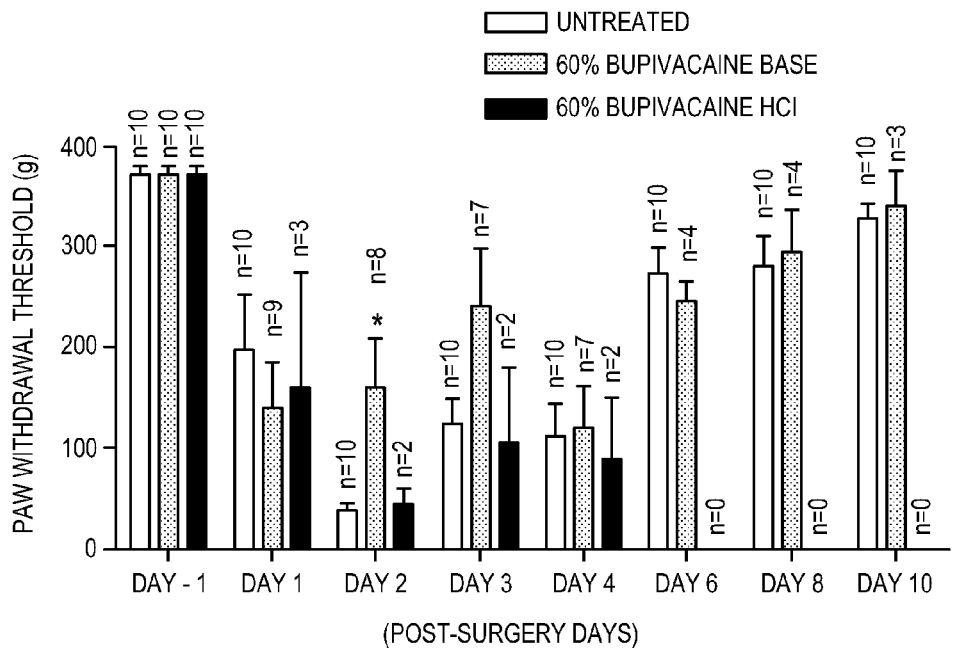
FIG. 7 is a graphic representation of mechanical hyperalgesia in bupivacaine treated animals.

FIG. 7 shows an in vivo efficacy evaluation of bupivacaine 1 and bupivacaine 2 formulations as measured by a paw withdrawal threshold in grams as measure at day 1, day 2, day 3, day 4, day 6, day 8 and day 10 post-surgery. These measurements are indicative of mechanical hyperalgesia in bupivacaine treated animals. Starting two days after the depot was implanted, there was a significant decrease in pain (indicated by the *).

The results for the clonidine formulations are summarized below in Table 2.

TABLE 2

| | | Clonidine | | | | |
|---|---|---|---|---|---|---|
| Formulation Number | Polymer | Active Wt. % of Clonidine | Excipient | Handling Property | In vitro elution profile | In vivo data |
| clonidine 1 (elution profile shown in FIGS. 5 and 6) | 85% PLGA 5050 1A | 5% (clonidine HCl) | 10% mPEG | Malleable | Day 1 release of 18%. By day 9 100% release. | Statistically significant reduction in mechanical hyperalgesia on D2 and D3. |
| clonidine 2 (elution profile shown in FIGS. 5 and 6) | 85% PLGA 5050 1A | 2.5% (clonidine HCl) | 10% mPEG | Malleable | Day 1 release of 22%. By day 9 100% release. | Statistically significant reduction in mechanical hyperalgesia on D2, D3 and D4. |

Figure 3:
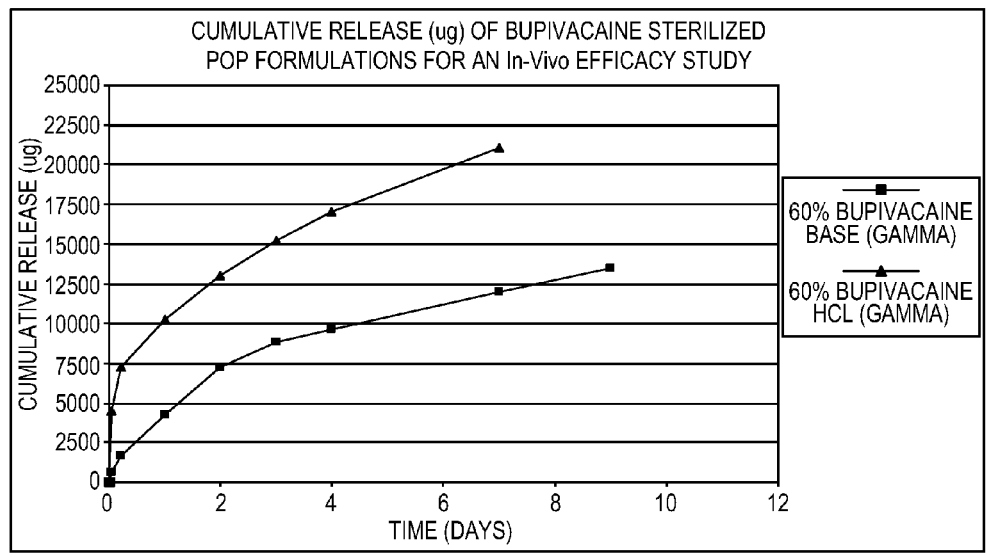
FIG. 3 is a graphic representation of a study of the cumulative release in ug of bupivacaine sterilized POP formulations for an in vivo efficacy study. (POP refers to post-operative pain.)
Figure 4:
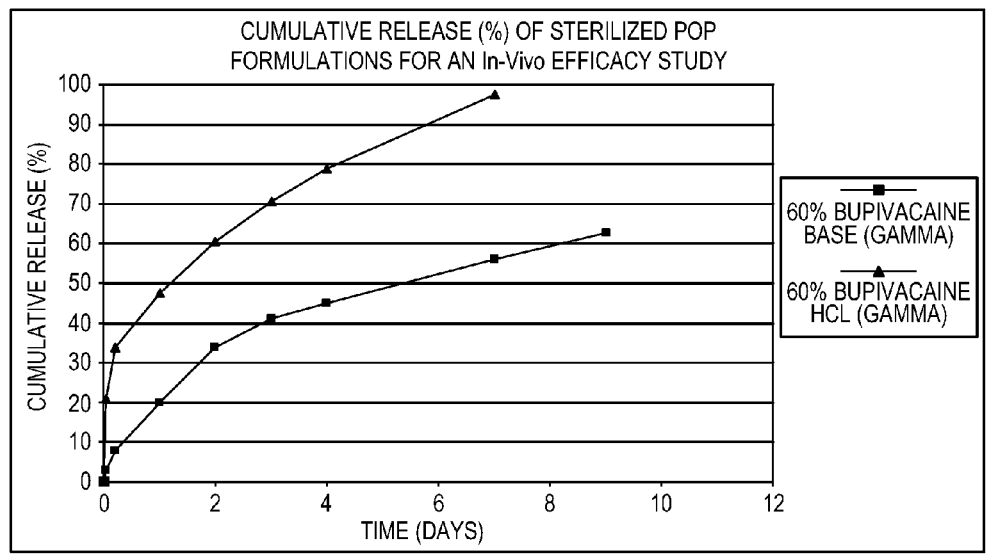
FIG. 4 is a graphic representation of a study of the percentage cumulative release of sterilized bupivacaine POP formulations for an in vivo efficacy study.

FIG. 3 is a graphic representation of a study of the cumulative release in ug of bupivacaine sterilized POP formulations for an in vivo efficacy study. In FIG. 3 the bupivacaine HCl released faster (over 2000 mcg in 7 days) than the bupivacaine base (slower over 12500 mcg over 9 days). FIG. 4 is a graphic representation of a study of the percentage cumulative release of sterilized bupivacaine POP formulations for an in vivo efficacy study. In FIG. 4 the bupivacaine HCl released faster (almost 100% in 7 days) than the bupivacaine base (slower over 60% over 9 days).

Figure 5:
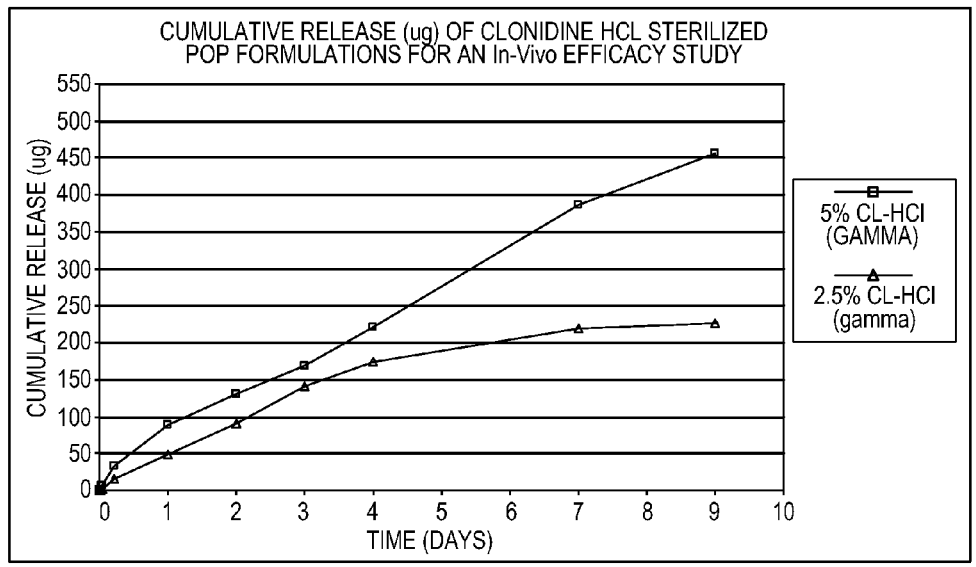
FIG. 5 is a graphic representation of a study of the cumulative release in ug of clonidine HCl sterilized POP formulations for an in vivo efficacy study.

For the bupivacaine 1 and 2 formulations, the polymer degraded in less than one month. The handling was of a nature to enable a malleable and formable formulation product that could be extruded to ribbon (strip)-like dosage forms. As a preliminary evaluation, the efficacy of these implant formulations was tested in the Brennan rate model of post-incisional pain. Mechanical hyperalgesia was used as the behavioral endpoint to assess the presence/absence of pain in the animal model following treatment with these drug formulations. The Brennan rat incision is made on the plantar aspect of the rat paw. The depth and length of the incision was a limiting factor in this model as the implant size was a bit bigger for the incision and became bulky in the rat's paw following implantation. This in turn affected wound healing. Some implants were lost from the incised paw at different time points following administration. Some animals were excluded from the study due to the loss of implants; evaluation of the efficacy of those formulations with the few remaining rats was not possible. However, of the few rats that proceeded through the study, the inventors noted a statistically significant reduction in mechanical hyperalgesia on day 2 post-surgery, following FIG. 5 is a graphic representation of a study of the cumulative release in ug of clonidine HCl sterilized POP formulations for an in vivo efficacy study. In FIG. 5 the 5 wt % clonidine HCl released faster (over 450 mcg in 9 days) than the 2.5 wt % clonidine HCl (over 200 mcg over 9 days). The more wt % drug load, the greater the release.

Figure 6:
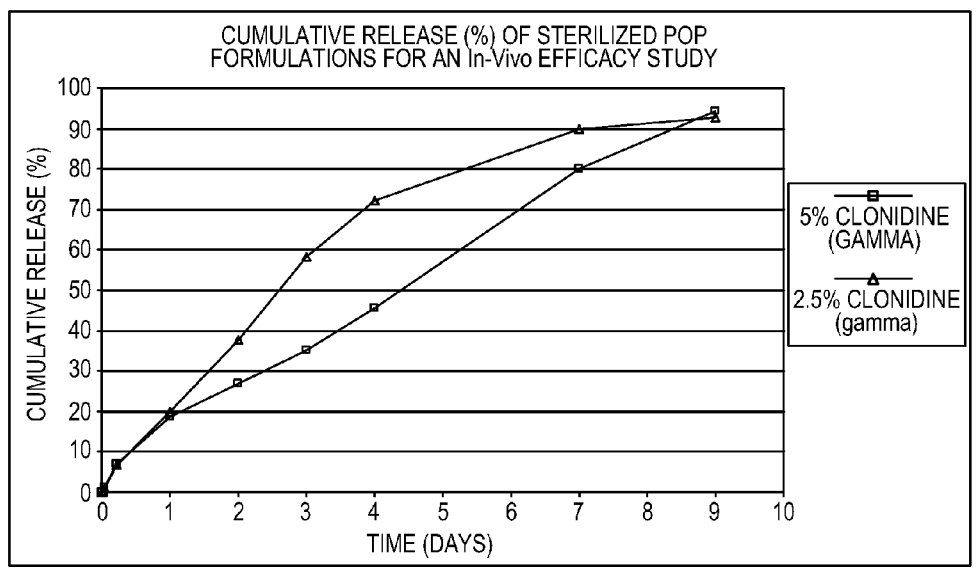
FIG. 6 is a graphic representation of a study of the cumulative release by percentage of clonidine HCl sterilized POP formulations for an in vivo efficacy study.

FIG. 6 is a graphic representation of a study of the cumulative release by percentage of clonidine HCl sterilized POP formulations for an in vivo efficacy study. In FIG. 6 the 2.5 wt % clonidine HCl released faster (over 90% from the drug depot in 9 days) than the 5 wt % clonidine HCl (over 90% from the drug depot in 9 days).

For both the clonidine 1 and 2 formulations, the polymer degraded in less than one month and the handling was of a malleable and formable product that could be extruded to ribbon-like (strip) dosage form. The efficacy of each of clonidine 1 and clonidine 2 were tested in the Brennan rat model of post-incisional pain. Mechanical hyperalgesia was used as the behaviorally endpoint to assess the presence/absence of pain the animal model following treatment with these drug formulations. Clonidine 1 showed statistically significant reduction in mechanical hyperalgesia on days 2 and 3 following its administration when compared to Brennan rats receiving no treatment. Whereas, clonidine 2 showed statistical reversal in mechanical hyperalgesia on days 2, 3 and 4. This preliminary in vivo study has demonstrated that both clonidine 1 and 2 formulations are effective in treating post-incisional pain in the Breen rat as assessed by the rats' behavioral responses to mechanical stimuli following treatment with the clonidine implants.

Figure 8:
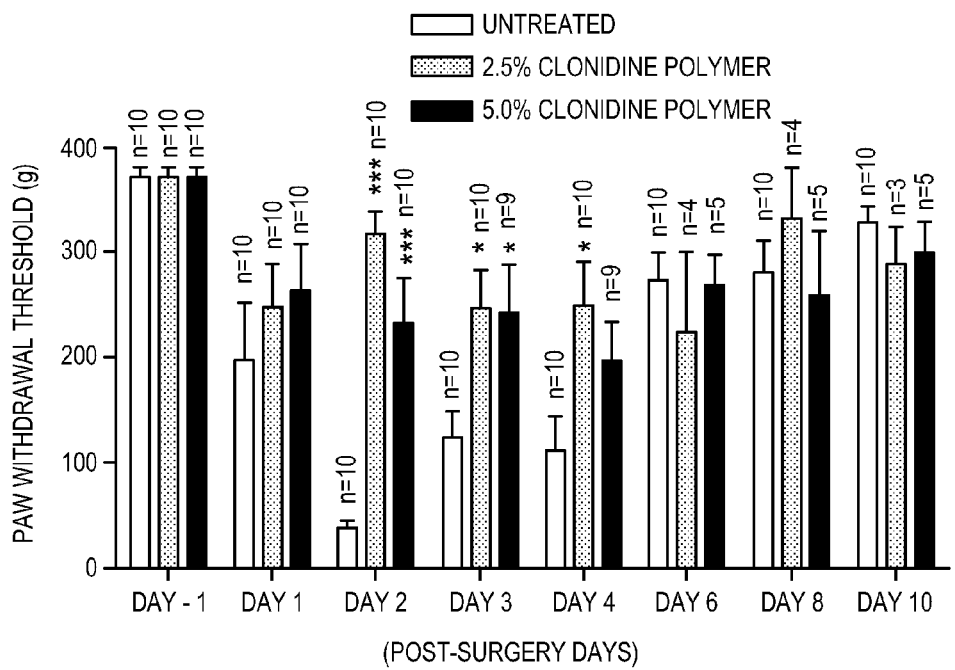
FIG. 8 is a graphic representation of mechanical hyperalgesia in clonidine treated animals.

FIG. 8 shows an in vivo efficacy evaluation of clonidine 1 and clonidine 2 formulations as measured by a paw withdrawal threshold in grams as measure at day 1, day 2, day 3, day 4, day 6, day 8 and day 10 post-surgery. These measurements are indicative of mechanical hyperalgesia in clonidine treated animals. Starting two days after the depot was implanted, there was a significant decrease in pain (indicated by the *).

Example 5

Figure 12A:
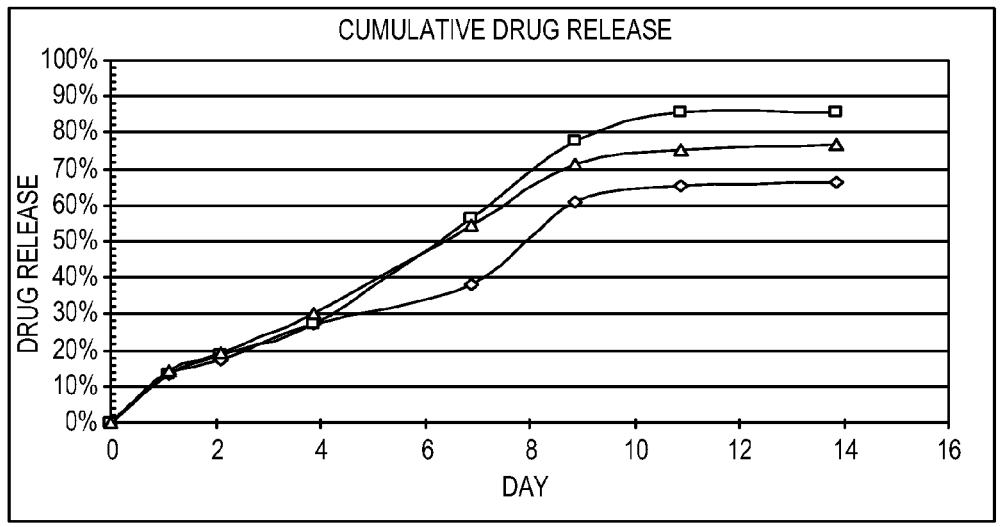
FIGS. 12A-12B are in vitro graphic representations of studies of the percentage cumulative release of sterilized bupivacaine in strip form of three formulations and its cumulative average release of the three formulations.
Figure 12B:
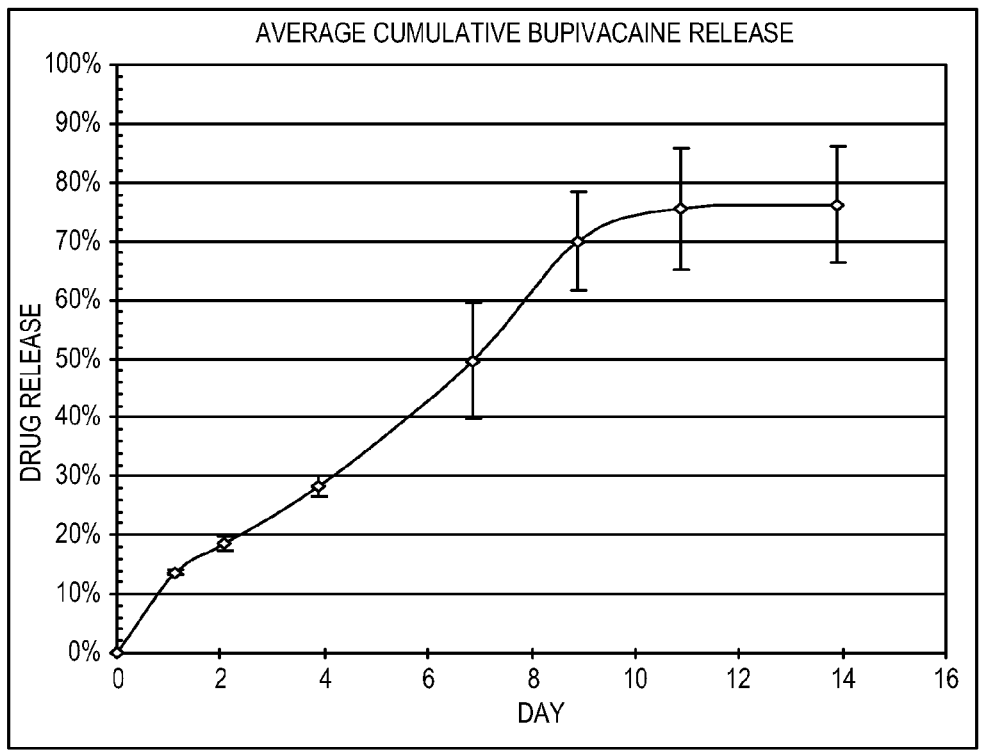

A drug depot was formulated as a strip. The formulation contained 50 wt % bupivacaine base, 42 wt % 5050DLG 1A, and 8 wt % mPEG. The inherent viscosity of the 5050DLG was 0.05-0.15 and had an acid end group. The in vitro cumulative and daily release profile was tested before sterilization for three of the same formulations. FIGS. 12A-12B are in vitro graphic representations of studies of the percentage cumulative release of sterilized bupivacaine in strip form of three formulations and its cumulative average release of the three formulations. Each formulation released between 65% to 85% of the bupivacaine over 14 days with an average of 5%-10% of drug released every day. The average cumulative drug release of the three formulations is shown in FIG. 12B, where 75% of the drug released in 14 days.

Figure 13A:
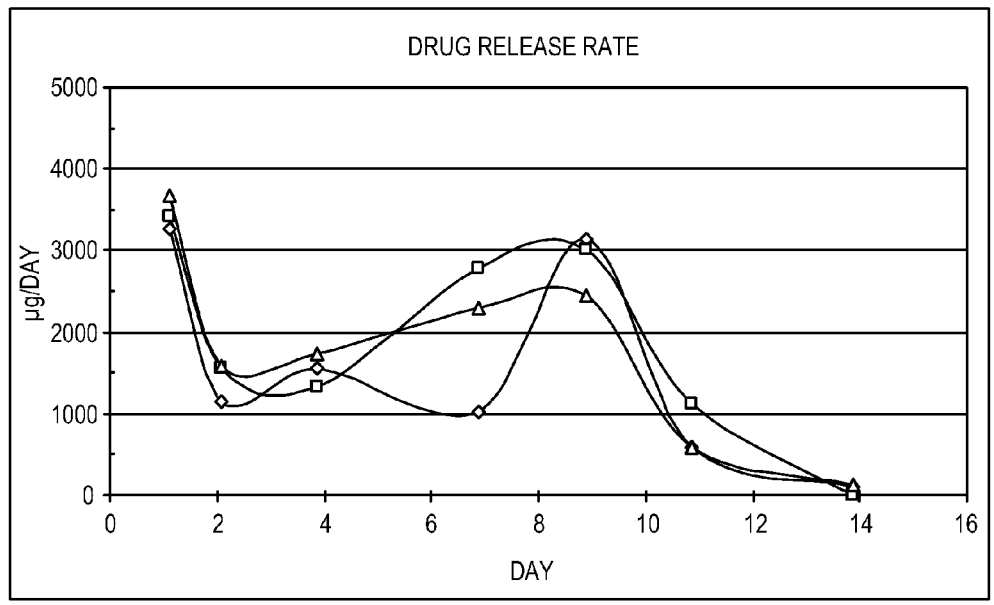
FIGS. 13A-13B are in vitro graphic representations of studies of the percentage daily release profiles of sterilized bupivacaine in strip form of three formulations and its cumulative average daily release of the three formulations in micrograms per day.
Figure 13B:
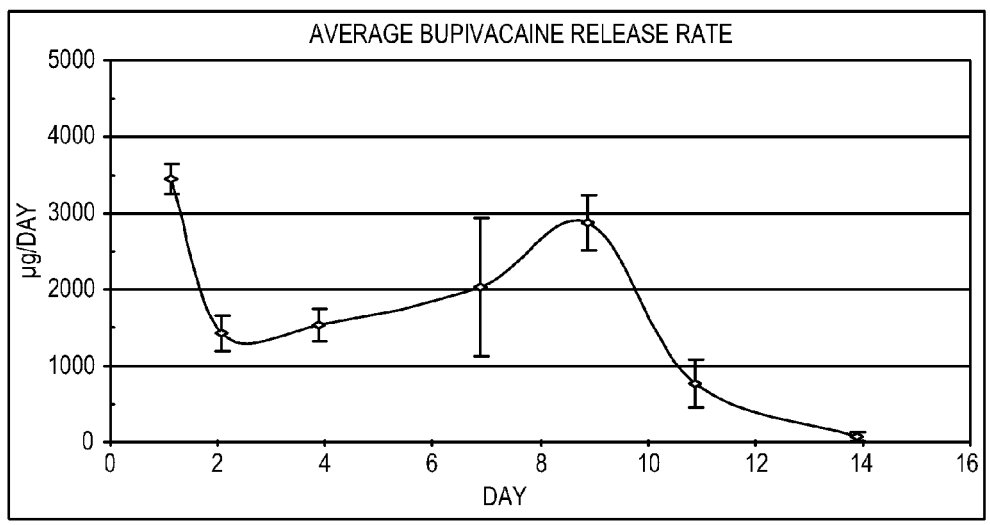

FIGS. 13A-13B are in vitro graphic representations of studies of the percentage daily release profiles of sterilized bupivacaine formulations of Example 5 in strip form of the three formulations and its cumulative average daily release of the three formulations in micrograms per day. Each drug depot had an initial burst effect with a release of bupivacaine at a dose of about 3500 mcg within 2 days. After the two days, the drug depot released about 500-1000 mcg per day until the drug depot was exhausted at day 14.

Example 6

A drug depot was formulated as a strip. The formulation contained 0.5 wt % clonidine HCl, which was spray dried, 25 wt % 5050DLG 4A, 64.5 wt % 5050 DLG 1A and 10 wt % mPEG, which was used as a plasticizer. The inherent viscosity of the 5050DLG was 0.35-0.45 and had an acid end group. The inherent viscosity of the 5050DLG was 0.05-0.15 and had an acid end group.

Figure 14A:
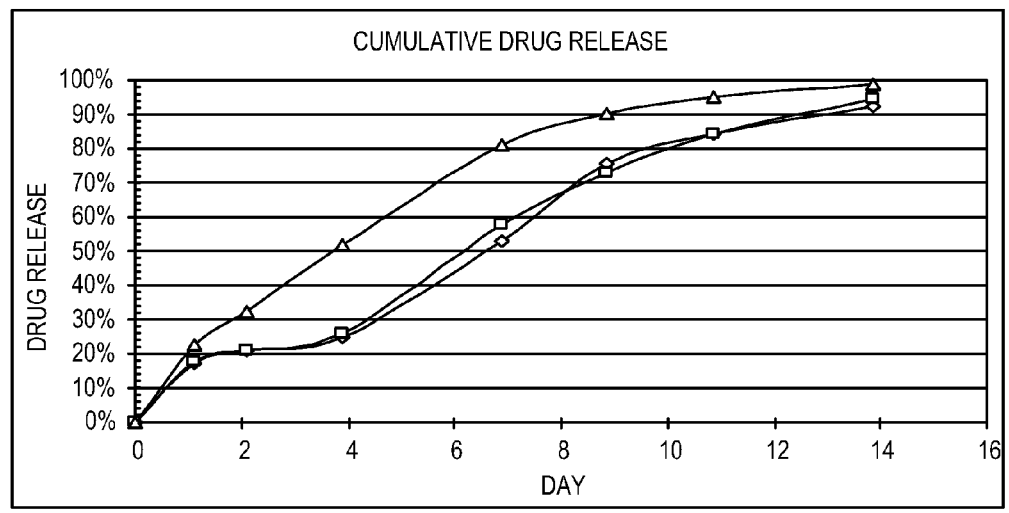
FIGS. 14A-14B are in vitro graphic representations of studies of the percentage cumulative release of sterilized clonidine HCl in strip form of three formulations and its cumulative average release of the three formulations.
Figure 14B:
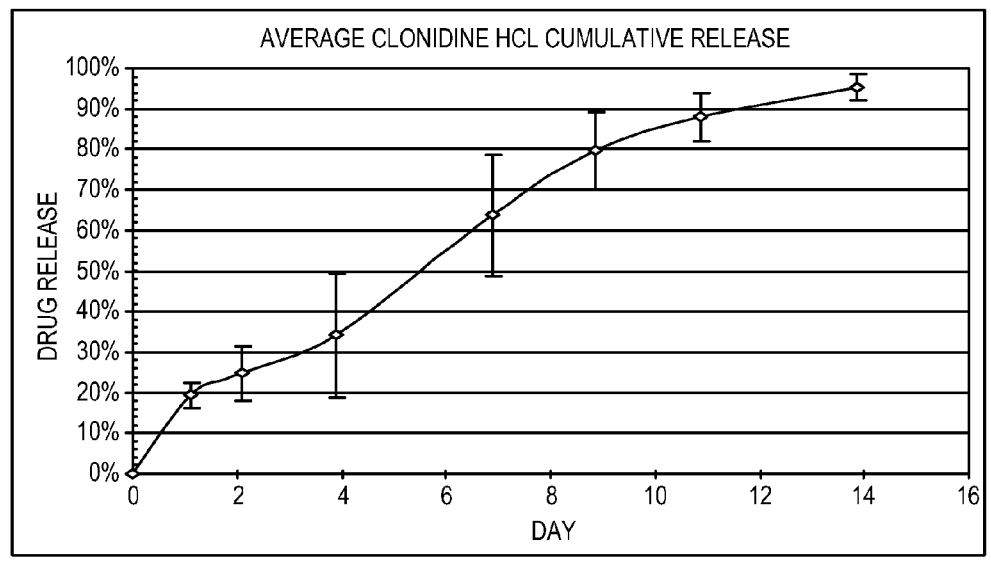

The in vitro cumulative and daily release profile was tested before sterilization for three of the same formulations. FIGS. 14A-14B are in vitro graphic representations of studies of the percentage cumulative release of sterilized clonidine in strip form of three formulations and its cumulative average release of the three formulations. Each formulation released between 90% to 100% of the clonidine over 14 days with an average of 5%-10% of drug released every day. The average cumulative drug release of the three formulations is shown in FIG. 14B, where 95% of the drug released in 14 days.

Figure 15A:
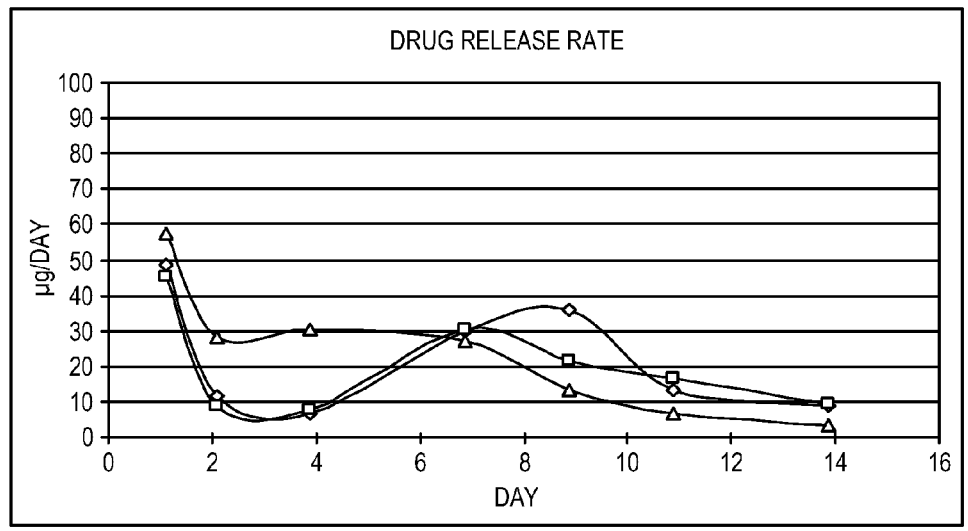
FIGS. 15A-15B are in vivo graphic representations of studies of the percentage daily release profiles of clonidine HCl in strip form of three formulations and its cumulative average daily release of the three formulations in micrograms per day.
Figure 15B:
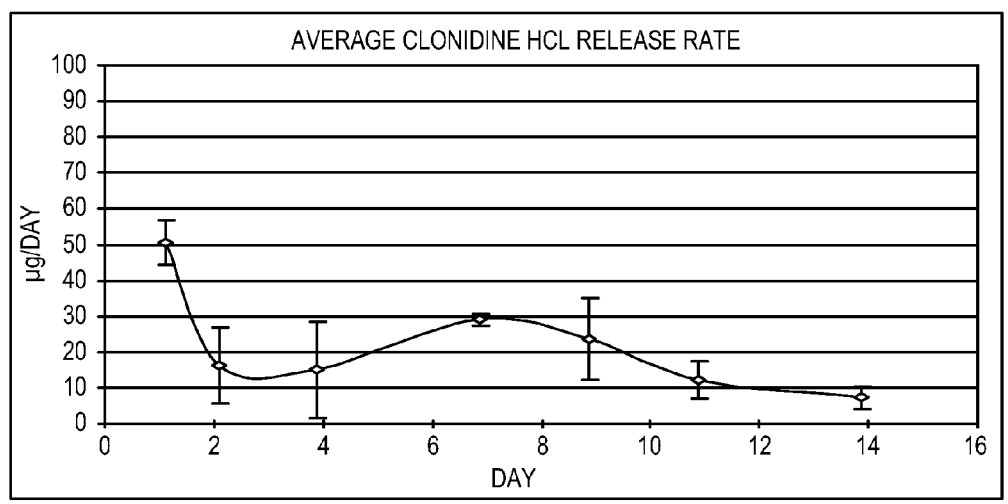

FIGS. 15A-15B are in vivo graphic representations of studies of the percentage daily release profiles of clonidine formulations of Example 6 in strip form of the three formulations and its cumulative average daily release of the three formulations in micrograms per day in vivo in a pig model. Each drug depot had an initial burst effect with a release of clonidine HCl at a dose of about 45 to 60 mcg within about 1 day. After the two days, the drug depot released about 5-15 mcg per day of clonidine until the drug depot was exhausted at day 14.

Example 7

In Vivo Efficacy Evaluation of Bupivacaine and Clonidine Implants in the Pig Surgical Model Induction of Post Operative Pain in piglets: Piglets were anesthetized by Isoflurane/Oxygen mixture, which was delivered through a face mask. A 5 cm long skin and fascia incision was made to the right femur at the groin keeping the muscle intact. The skin incision was closed with metal clamps. The duration of the anesthesia was kept at less than 10 minutes. Immediately after the incision, the animals were administered with either control or drug implants into the incisional space. Morphine (Mor) was administered subcutaneously in the animals in the morphine group as a positive control.

Analgesia evaluation: The analgesic effect of clonidine and bupivacaine implants were assessed using pain behavior scoring. The pain scoring system was the summation of 3 major categories:
1. Animal solitary performance (walking and vocalization)
2. Animal social behavior
3. The length of time in which the pigs stayed on a sling All animals were observed at baseline (3 days prior to surgery) and 1 and 3 hours post surgery (study day 0). Pain behavior was then assessed daily for 4 more days (study days 1, 2, 3 and 4). The implants were administered into the surgical wound bed on study day 0 immediately right after surgery. Morphine was administered one hour prior to pain assessment in animals in the morphine group (Mor).

Figure 16:
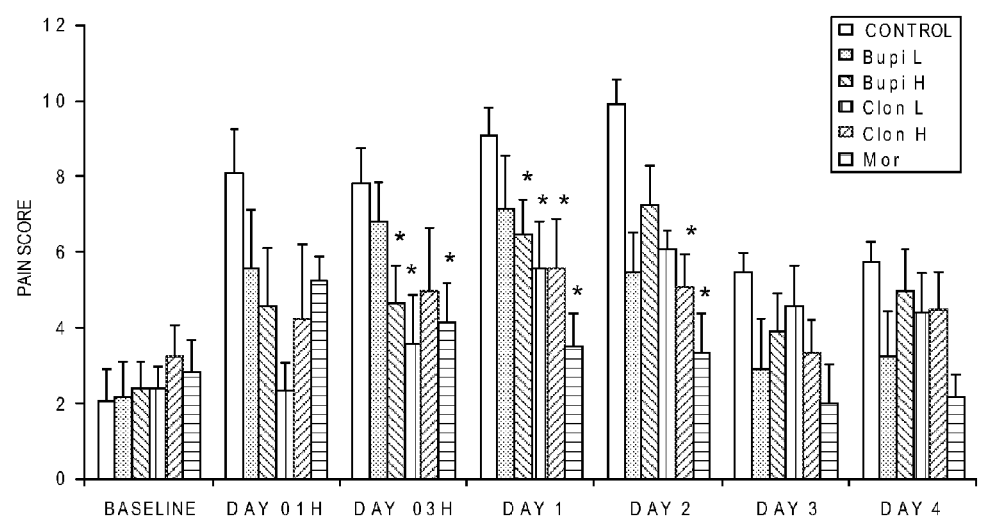
FIG. 16 is a graphic representation of pain scores of implanted clonidine and bupivacaine depots implanted postoperatively at the surgical incision.

Results: FIG. 16 shows an in vivo efficacy evaluation of clonidine high dose (1500 mcg loaded in the depot designed to release about 150 mcg/day) and bupivacaine high dose (250 mcg loaded in the depot, designed to release 25 mcg/day) formulations and clonidine (750 mcg loaded in the depot designed to release about 75 mcg/day) and bupivacaine low dose (125 mcg loaded in the depot, designed to release 12.5 mcg/day) formulations as measured by pain scores at 1 hour, 3 hours, day 1, day 2, day 3, and day 4, post-surgery. The increase in the pain behavior score reached a peak at 3 hours post surgery on study day 0 (control group: 7.83±0.9 points). The high mean group pain score of the control treated animals was observed also on study day 1. On study day 2 spontaneous recovery of pain behavior was observed and 4 days post surgery the pain behavior score was not statistically different from baseline value.

Treatment with bupivacaine implants using high level or clonidine implants was effective in reducing pain 3 hours post surgery and 1 day post surgery (as indicated by the asterisks). This effect was not dose related (see graph below).

Conclusion: In view of the findings obtained under the conditions of this study and confined to the in-life data, treatment with bupivacaine implants at high levels and clonidine implants were effective in reducing post operative pain in pigs.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for localized delivery to a site beneath the skin of a patient, the drug depot comprising: a therapeutically effective amount of bupivacaine or pharmaceutically acceptable salt thereof and clonidine or pharmaceutically acceptable salt thereof, wherein the drug depot is capable of releasing the bupivacaine or pharmaceutically acceptable salt thereof and clonidine or pharmaceutically acceptable salt thereof over a period of at least one day, wherein the bupivacaine is in the form of a base and the clonidine is in the form of a salt and the drug depot has a modulus of elasticity of about $2 \times 10^4$ to about $5 \times 10^5$ dynes/cm$^2$, and wherein the drug depot comprises a polymer having an inherent viscosity of from about 0.10 dL/g to about 1.2 dL/g, and the ratio of clonidine to bupivacaine is about 1:5, and wherein the drug depot further comprises a plasticizer comprising mPEG.

2. An implantable drug depot of claim 1, wherein the polymer is PLGA or POE.

3. An implantable drug depot of claim 1, wherein the bupivacaine is in the form of a salt and the clonidine is in the form of a salt.

4. An implantable drug depot useful for treating postoperative pain or inflammation in a patient in need of such treatment, the implantable drug depot comprising the drug depot of claim 1, the drug depot being implantable at a site beneath the skin to prevent or treat postoperative pain, wherein the drug depot releases an effective amount of bupivacaine or pharmaceutically acceptable salt thereof and clonidine or pharmaceutically acceptable salt thereof over a period of 3 to 12 days, wherein the bupivacaine is in the form of a base and the clonidine is in the form of a salt and the drug depot has a modulus of elasticity of about $2 \times 10^4$ to about $5 \times 10^5$ dynes/$cm^2$, and wherein the drug depot comprises a polymer having an inherent viscosity of from about 0.10 dL/g to about 1.2 dL/g, and the ratio of clonidine to bupivacaine is about 1:5, and wherein the drug depot further comprises a plasticizer comprising mPEG.

5. A method of treating or inhibiting postoperative pain or inflammation in a patient in need of such treatment, the method comprising administering one or more biodegradable drug depots comprising the drug depot of claim 1 to a target tissue site beneath the skin, wherein the drug depot releases an effective amount of said bupivacaine or pharmaceutically acceptable salt thereof and said clonidine or pharmaceutically acceptable salt thereof over a period of 3 to 12 days.

6. A method of treating or inhibiting postoperative pain or inflammation according to claim 5, wherein one or more drug depots release an effective amount of bupivacaine or pharmaceutically acceptable salt thereof and clonidine or pharmaceutically acceptable salt thereof over a period of 5 to 10 days.

7. A method of treating or inhibiting postoperative pain or inflammation according to claim 5, wherein the drug depot releases 5%, 10%, 15%, 20%, 25%, 30%, 40%, 50%, 60%, 70%, 80%, 90%, 95%, or 99% of the bupivacaine or pharmaceutically acceptable salt thereof and clonidine or pharmaceutically acceptable salt thereof relative to a total amount of bupivacaine or pharmaceutically acceptable salt thereof and clonidine or pharmaceutically acceptable salt thereof loaded in the drug depot over a period of 3 to 10 days after the drug depot is administered to the target tissue site.

8. A method of treating or inhibiting postoperative pain or inflammation according to claim 5, wherein the drug depot releases 5 mg to 60 mg of bupivacaine or pharmaceutically acceptable salt thereof and 10 μg to 100 μg of clonidine or pharmaceutically acceptable salt thereof every 4 to 6 hours to treat postoperative pain or inflammation.

9. A method of treating or inhibiting postoperative pain or inflammation according to claim 5, wherein the target tissue site comprises at least one muscle, ligament, tendon, cartilage, spinal disc, spinal foraminal space near the spinal nerve root, facet or synovial joint, or spinal canal.

10. A method of treating or inhibiting postoperative pain or inflammation according to claim 5, wherein the drug depot comprises at least one additional anti-inflammatory or analgesic agent, at least one anabolic or an anti-catabolic growth factor or a combination thereof.

11. A method of treating or inhibiting reventing postoperative pain or inflammation according to claim 5, wherein the bupivacaine or pharmaceutically acceptable salt thereof and clonidine or pharmaceutically acceptable salt thereof is encapsulated in a plurality of depots comprising microparticles, microspheres, microcapsules, and/or microfibers suspended in a gel.

12. A method of treating or inhibiting postoperative pain or inflammation according to claim 5, wherein the pain or inflammation is associated with orthopedic surgery, spine surgery, arthroscopic surgery, an excision of a mass, hernia repair, spinal fusion, thoracic, cervical, or lumbar surgery, pelvic surgery or a combination thereof.

13. A method of treating or inhibiting postoperative pain or inflammation according to claim 5, wherein the drug depot comprises a radiographic marker adapted to assist in radiographic imaging.

14. A method of treating or inhibiting postoperative pain or inflammation according to claim 13, wherein the radiographic marker comprises barium, bismuth, iodine, tantalum, tungsten, calcium, and/or metal beads.

15. A method of inhibiting postoperative pain or inflammation in a patient in need of such treatment, the method comprising delivering one or more biodegradable drug depots comprising the drug depot of claim 1 to a target tissue site beneath the skin before, during or after surgery, wherein the drug depot releases an effective amount of bupivacaine or pharmaceutically acceptable salt thereof and clonidine or pharmaceutically acceptable salt thereof over a period of 3 to 12 days.

16. A method of inhibiting postoperative pain or inflammation according to claim 15, wherein one or more drug depots release an effective amount of bupivacaine or pharmaceutically acceptable salt thereof and clonidine or pharmaceutically acceptable salt thereof over a period of 5 to 10 days.

17. A method of inhibiting postoperative pain or inflammation according to claim 16, wherein the drug depot releases 5%, 10%, 15%, 20%, 25%, 30%, 40%, 50%, 60%, 70%, 80%, 90%, 95%, or 99% of bupivacaine or pharmaceutically acceptable salt thereof and clonidine or pharmaceutically acceptable salt thereof relative to a total amount of bupivacaine or pharmaceutically acceptable salt thereof and clonidine or pharmaceutically acceptable salt thereof loaded in the drug depot over a period of 3 to 10 days after the drug depot is administered to the target tissue site.

18. A method of treating or inhibiting postoperative pain or inflammation in a patient in need of such treatment, the method comprising co-administering a first biodegradable drug depot of claim 1 and a second biodegradable drug depot of claim 1 to a target site, wherein said first biodegradable drug depot releases an effective amount of said bupivacaine or pharmaceutically acceptable salt thereof over a period of 3 to 12 days and wherein said second biodegradable drug depot releases clonidine or pharmaceutically acceptable salt thereof over a period of 3 to 12 days.

* * * * *

UNITED STATES PATENT AND TRADEMARK OFFICE
CERTIFICATE OF CORRECTION

PATENT NO. : 9,132,085 B2  
APPLICATION NO. : 12/420110  
DATED : September 15, 2015  
INVENTOR(S) : McDonald et al.

Page 1 of 1

It is certified that error appears in the above-identified patent and that said Letters Patent is hereby corrected as shown below:

On Title Page 2, in Item (56), under "OTHER PUBLICATIONS", in Column 2, Line 12, delete "QLT," and insert -- QLT --, therefor.

In the Drawings

In Fig. 11a, Sheet 8 of 13, delete "25% Bupiv. Base:" and insert -- 25% Bupiv. Base; --, therefor.

In the Specification

In Column 1, Line 66, delete "($C_9H_9C1_2N_3$)" and insert -- ($C_9H_9Cl_2N_3$) --, therefor.

In Column 2, Line 15, delete "($C_{18}H_{28}N_2O$))" and insert -- ($C_{18}H_{28}N_2O$) --, therefor.

In Column 11, Line 36, delete "$2 \times 105$ to about $5 \times 10^5$ dyne/cm$^2$." and insert -- $2 \times 10^5$ to about $5 \times 10^5$ dynes/cm$^2$. --, therefor.

In the Claims

In Column 36, Line 4, in Claim 11, delete "inhibiting reventing" and insert -- inhibiting --, therefor.

Signed and Sealed this  
Twenty-eighth Day of June, 2016

Michelle K. Lee  
*Director of the United States Patent and Trademark Office*